US006258529B1

(12) United States Patent
Berdoz et al.

(10) Patent No.: US 6,258,529 B1
(45) Date of Patent: *Jul. 10, 2001

(54) PCR AMPLIFICATION OF REARRANGED GENOMIC VARIABLE REGIONS OF IMMUNOGLOBULIN GENES

(75) Inventors: José Berdoz, La Tour-de-Peilz; Jean-Pierre Kraehenbuhl, Rivaz, both of (CH)

(73) Assignee: OraVax, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/348,548

(22) Filed: Dec. 1, 1994

(51) Int. Cl.[7] .............................. C12Q 1/68; C12P 21/06; C07H 21/04
(52) U.S. Cl. ...................... 435/6; 435/69.1; 536/23.53
(58) Field of Search ................ 536/23.53; 435/69.1, 435/6

(56) References Cited

U.S. PATENT DOCUMENTS

| | | | |
|---|---|---|---|
| 4,816,397 | 3/1989 | Boss et al. | 435/86 |
| 5,534,411 | * 7/1996 | Weltzin | 435/7.2 |

FOREIGN PATENT DOCUMENTS

| | | |
|---|---|---|
| WO 93/20210 | * 10/1993 | (GB) . |
| 04141095 | 5/1992 | (JP) . |
| WO 95/04081 | 2/1995 | (WO) . |

OTHER PUBLICATIONS

Garcia–Barreno et al., Marked Differences in the Antigenic Structure of Human Respiratory Syncytial Virus F and G Glycoproteins, Journal of Virology, 63:925–932, 1994.

Tempest et al., Reshaping a Human Monoclonal Antibody to Inhibit Human Respiratory Syncytial Virus Infection In Vivo, Bio/Technology, 9:266–271, 1991.

Scott et al., Respiratory Syncytial Virus Neutralizing Activity in Nasopharyngeal Secretions, Journal Hyg. Camb. 68:581–588, 1970.

Benoist & Chambon, In vivo Sequence Requirements of the SV40 Early Promoter Region, Nature 290:304–310, 1981.

Boulianne et al., Production of Functional Chimaeric Mouse/Human Antibody, Nature 312:643–646, 1984.

Carroll et al., Hybridoma Fusion Cell Lines Contain an Aberrant Kappa Transcript, Molecular Immunology 25:991–995, 1988.

Chirgwin et al., Isolation of Biologically Active Ribonucleic Acid from Sources Enriched in Ribonuclease, Biochemistry 18:5294–5299, 1979.

Chomczynski and Qasba, Alkaline Transfer of DNA to Plastic Membrane, Biochem. Biophys. Res. Comm. 122:340–344, 1984.

Chothia et al., Conformations of Immunoglobulin Hypervariable Regions, Nature 342:877–883, 1989.

Co and Queen, Humanized Antibodies for Therapy, Nature 351:501–502, 1991.

DeBernardi et al., Inhibition of cAMP Accumulation by Intracellular Calcium Mobilization in C6–2B Cells Stably Transfected with Substance K Receptor cDNA, Proc. Natl. Acad. Sci. USA 88:9257–9261, 1991.

(List continued on next page.)

*Primary Examiner*—Hankyel T. Park
(74) *Attorney, Agent, or Firm*—Clark & Elbing, LLP

(57) ABSTRACT

The invention features methods for isolating immunoglobulin variable region genes, and the use of these genes in the production of chimeric and isotype switched antibodies. The invention also features substantially pure DNA encoding a variable region of the antibody produced by hybridoma cell line HNK-20, and chimeric antibodies containing this variable region.

5 Claims, 12 Drawing Sheets

OTHER PUBLICATIONS

Figure 1A:
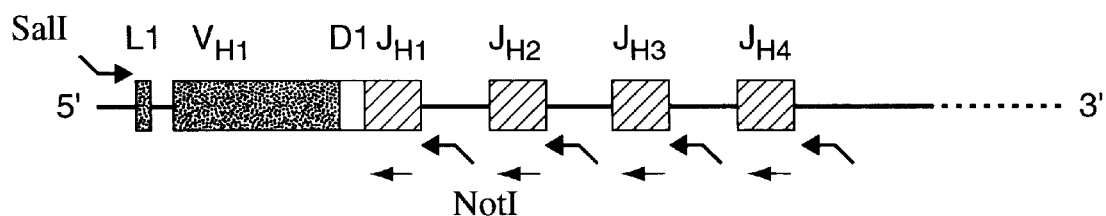

Gavilondo–Cowley et al., Specific Amplification of Rearranged Immunoglobulin Variable Region Genes from Mouse Hybridoma Cells, Hybridoma 9:407–417, 1990.

Glisin et al., Ribonucleic Acid Isolated by Cesium Chloride Centrifugation, Biochemistry 13:2633–2637, 1974.

Gross–Bellard et al., Isolation of High–Molecular–Weight DNA from Mammalian Cells, Eur. J. Biochem. 36:32–38, 1973.

Hamer and Walling, Regulation In Vivo of a Cloned Mammalian Gene: Cadmium Induces the Transcription of a Mouse Metallothionein Gene in SV40 Vectors, J. Mol. Appl. Genet. 1:273–288, 1982.

Jones et al., Replacing the Complementarity–Determining Regions in a Human Antibody with Those from a Mouse, Nature 321:522–525, 1986.

Jones and Bendig, Rapid PCR–Cloning of Full–Length Mouse Immunoglobulin Variable Regions, Bio/Technology 9:88–89, 1991.

Kaluza et al., A General Method for Chimerization of Monoclonal Antibodies by Inverse Polymerase Chain Reaction which Conserves Authentic N–terminal Sequences, Gene 122:321–328, 1992.

Kettleborough et al., Optimization of Primers for Cloning Libraries of Mouse Immunoglobulin Genes Using the Polymerase Chain Reaction, Eur. J. Immunol. 23:206–211, 1993.

LeBoeuf et al., Cloning and Sequencing of Immunoglobulin Variable–Region Genes Using Degenerate Oligodeoxy–ribonucleotides and Polymerase Chain Reaction, Gene 82:371–377, 1989.

Leung et al., An Extended Primer Set for PCR Amplification of Murine Kappa Variable Regions, BioTechniques 15:286–292, 1993.

Liu et al., Expression of Mouse::Human Immunoglobulin Heavy–chain cDNA in Lymphoid Cells, Gene 54:33–40, 1987.

McKnight, Functional Relationships Between Transcriptional Control Signals of the Thymidine Kinase Gene of Herpes Simplex Virus, Cell 31:355–365, 1982.

McMaster et al., Analysis of Single– and Double–stranded Nucleic Acids on Polyacrylamide and Agarose Gels by Using Glyoxal and Acridine Orange, Proc. Natl. Acad. Sci. USA 74:4835–4838, 1977.

Morrison et al., Chimeric Human Antibody Molecules: Mouse Antigen–binding Domains with Human Constant Region Domains, Proc. Natl. Acad. Sci. USA 81:6851–6855, 1984.

Ochi et al., Functional Immunoglobulin M Production After Transfection of Cloned Immunoglobulin Heavy and Light Chain Genes into Lymphoid Cells, Proc. Natl. Acad. Sci. USA 80:6351–6355, 1983.

Orlandi et al., Cloning Immunoglobulin Variable Domains for Expression by the Polymerase Chain Reaction, Proc. Natl. Acad. Sci. USA 86:3833–3837, 1989.

Piechaczyk et al., Post–transcriptional Regulation of Glyceraldehyde–3–phosphate–dehydrogenase Gene Expression in Rat Tissues, Nucleic Acids Research 12:6951–6963, 1984.

Ratech et al., Sensitive Detection of Clonal Antigen Receptor Gene Rearrangements in Non–Hodgkin's Malignant Lymphoma with an Anchored Polymerase Chain Reaction-–based Strategy, Am. J. Clin. Pathol. 100:527–533, 1993.

Sanger et al., DNA Sequencing with Chain–terminating Inhibitors, Proc. Natl. Acad. Sci. USA 74:5463–5467, 1977.

Storb et al., Myeloma with Multiple Rearranged Immunoglobulin Kappa Genes: Only One Kappa Gene Codes for Kappa Chains, Nucleic Acids Research 8:4681–4687, 1980.

Strohal et al., Complete Variable Region Sequence of a Nonfunctionally Rearranged Kappa Light Chain Transcribed in the Nonsecretor P3–X63–Ag8.653 Myeloma Cell Line, Nucleic Acids Research 15:2771–2776, 1987.

Weissenhorn et al., Chimerization of Antibodies by Isolation of Rearranged Genomic Variable Regions by the Polymerase Chain Reaction, Gene 106:273–277, 1991.

Altenburger et al., "Functional and Non–functional Joining Immunoglobulin Light Chain Genes of a Mouse Myeloma," Nature 287:603–607 (1980).

Berdoz et al., "Specific Amplification by PCR of Rearranged Genomic Variable Regions of Immunoglobulin Genes from Mouse Hybridoma Cells," PCR Methods and Applications 4:256–264 (1995).

Johnson et al., "Development of Humanized Monoclonal Antibodies Which Neutralize Respiratory Syncytial Virus," Journal of Cellular Biochemistry 15:120 Abstract (1991).

Nahmias et al., "The Immune Response Toward β–Adrenergic Ligands and Their Receptors," The Journal of Immunology 140:1304–1311 (1988).

Weltzin et al., "Intranasal Monoclonal Immunoglobulin A Against Respiratory Syncytial Virus Protects Against Upper and Lower Respiratory Tract Infections in Mice," Antimicrobial Agents and Chemotherapy 38:2785–2791 (1994).

OraVax Inc., Cambridge, MA, 1996 Annual Report, pp. 2, 10, and 11.

OraVax Inc., Mar. 19, 1997, Press Release: "OraVax Reports Results from Phase III Trial of HNK20 Nosedrop for Respiratory Syncytial Virus in Infants".

* cited by examiner

```
     GATCGTCGACCGTGGTTTGTGAATTATG GCC TGG ATT TCA CTT ATA CTC TCT CTC    55
                                 Met Ala Trp Ile Ser Leu Ile Leu Ser Leu  10

CTG GCT CTC AGC TCA G GTCAGCAGCCTTTCTACACTGCAGTGGGTATGCAACAATGCGCAT     116
Leu Ala Leu Ser Ser G                                                    15

CTTGTCTCTGATTTGCTACTGATGACTGGATTTCTCATCTGTTTGCAG GG GCC ATT TCC CAG    178
                                                 ly Ala Ile Ser Gln     20

GCT GTT GTG ACT CAG GAA TCT GCA CTC ACC ACA TCA CCT GGT GAA ACA GTC    229
Ala Val Val Thr Gln Glu Ser Ala Leu Thr Thr Ser Pro Gly Glu Thr Val     37

ACA CTC ACT TGT CGC TCA AGT ACT GGG GCT GTT ACA ACT AGT AAC TAT GCC    280
Thr Leu Thr Cys Arg Ser Ser Thr Gly Ala Val Thr Thr Ser Asn Tyr Ala     54

AAC TGG GTC CAA GAA AAA CCA GAT CAT TTA TTC ACT GGT CTA ATA GGT GGT    331
Asn Trp Val Gln Glu Lys Pro Asp His Leu Phe Thr Gly Leu Ile Gly Gly     71

ACC AAC AAC CGA GCT CCA GGT GTT CCT GCC AGA TTC TCA CGC TCC CTG ATT    382
Thr Asn Asn Arg Ala Pro Gly Val Pro Ala Arg Phe Ser Gly Ser Leu Ile     88

GGA GAC AAG GCT GCC CTC ACC ATC ACA GGG GCA CAG ACT GAG GAT GAG GCA    433
Gly Asp Lys Ala Ala Leu Thr Ile Thr Gly Ala Gln Thr Glu Asp Glu Ala    105

ATA TAT TTC TGT GCT CTA TGG TAC AGC AAC CAT TGG GTG TTC GGT GGA GGA    484
Ile Tyr Phe Cys Ala Leu Trp Tyr Ser Asn His Trp Val Phe Gly Gly Gly    122

ACC AAA CTG ACT GTC CTA G GTGAGTCACTCCTCCCTCCTTTGCGGCCGCTGAT           537
Thr Lys Leu Thr Val Leu                                                128
```

Fig. 5A

```
GATCGTCGACGGACTCAGCATGGACATG AGG ACC CCT GCT CAG TTT CTT GGA ATC   55
                             Met Arg Thr Pro Ala Gln Phe Leu Gly Ile  10

TTG TTG CTC TGG TTT CCA G GTAAAATGAACTAAAATGGGAATGTCACTGTGATTAGTGTTG 116
Leu Leu Leu Trp Phe Pro G                                              16

ATTGGCATTTGGGAGATTTTATCTTTTATGATGCTTACCTATGTAGATACTCATTATGTCTCCATTC  183

CTAG GT ATC AAA TGT GAC ATC AAG GTG ACC CAG TCT CCA TCT TCC ATG TAT  234
     ly Ile Lys Cys Asp Ile Lys Val Thr Gln Ser Pro Ser Ser Met Tyr   32

GCA TCT CTA GGA GAG AGA GTC ACT ATC ACT TGC AAG GCG AGT CAG GAC ATT  285
Ala Ser Leu Gly Glu Arg Val Thr Ile Thr Cys Lys Ala Ser Gln Asp Ile   49

AAT AAC TAT TTA AAC TGG TTC CAG CAG AAA CCA GGG AAA TCT CCT AAG ACC  336
Asn Asn Tyr Leu Asn Trp Phe Gln Gln Lys Pro Gly Lys Ser Pro Lys Thr   66

CTG ATC TAT CGT GCA AAC AGA TTG CTA GAT GGG GTC CCA TCA AGG TTC AGT  387
Leu Ile Tyr Arg Ala Asn Arg Leu Leu Asp Gly Val Pro Ser Arg Phe Ser   83

GGC AGT GGA TCT GGG CAA GAT TAT TCT CTC ACC ATC AGC AGC CTG GAG TAT  438
Gly Ser Gly Ser Gly Gln Asp Tyr Ser Leu Thr Ile Ser Ser Leu Glu Tyr  100

GAA GAT ATG GGA ATT TAT TAT TGT CTA CAG TTT GAC GAG TTT CCG TAC ACG  489
Glu Asp Met Gly Ile Tyr Tyr Cys Leu Gln Phe Asp Glu Phe Pro Tyr Thr  117

TTC GGA GGG GGG ACC AAG CTG GAA ATA AAA C GTAAGTAGTCTTCTCAACTCTTGCG  545
Phe Gly Gly Gly Thr Lys Leu Glu Ile Lys                              127

GCCGCTGAT                                                             554
```

Fig. 5B

```
           GATCGTCGACTTCCAGCTCTCAGAGATG GAG ACA GAC ACA CTC CTG TTA TGG GTA    55
                                       Met Glu Thr Asp Thr Leu Leu Leu Trp Val   10

CTG CTG CTC TGG GTT CCA G GTGAGAGTGCAGAGAAGTGTTGGATGCAACCTCTGTGGCCA          115
Leu Leu Leu Trp Val Pro G                                                    16

TTATGATACTCCATGCCTCTCTGTTCTTGATCACTATAATTAGGGCATTTGTCACTGGTTTTAAGTT         182

TCCCCAGTCCCCTGAATTTTCCATTTCCTCAGAGTGATGTCCAAAATTCTTCTTAAAAATTTAAATC         249

AAAAGGTCCTCTGCTGTGAAGTCTTTTATACATATATAACAATAATCTTTGTGTTTATCATTCCAG          315

GT TCC ACT GGT GAC ATT GTG CTG ACA CAG TCT CCT GCT TCC TTA GCT GTA          365
 ly Ser Thr Gly Asp Ile Val Leu Thr Gln Ser Pro Ala Ser Leu Ala Val           33

TCT CTG GGG CAG AGG GCC ACC ATC TCA TAC AGG GCC AGC AAA AGT GTC AGT          416
Ser Leu Gly Gln Arg Ala Thr Ile Ser Tyr Arg Ala Ser Lys Ser Val Ser           50

ACA TCT GGC TAT AGT TAT ATG CAC TGG AAC CAA CAG AAA CCA GGA CAG CCA          467
Thr Ser Gly Tyr Ser Tyr Met His Trp Asn Gln Gln Lyn Pro Gly Gln Pro           67

CCC AGA CTC CTC ATC TAT CTT GTA TCC AAC CTA GAA TCT GGG GTC CCT GCC          518
Pro Arg Leu Leu Ile Tyr Leu Val Ser Asn Leu Glu Ser Gly Val Pro Ala           84

AGG TTC AGT GGC AGT GGG TCT GGG ACA GAC TTC ACC CTC AAC ATC CAT CCT          569
Arg Phe Ser Gly Ser Gly Ser Gly Thr Asp Phe Thr Leu Asn Ile His Pro          101

GTG GAG GAG GAG GAT GCT GCA ACC TAT TAC TGT CAG CAC ATT AGG CAG CTT          620
Val Glu Glu Glu Asp Ala Ala Thr Tyr Tyr Cys Gln His Ile Arg Glu Leu          118

ACA CGT TCG GAG GGG GGA CCA AGC TGG AAA TAA AAC GTAAGTAGTCTTCTCAACT          675
Thr Arg Ser Glu Gly Gly Pro Ser Trp Lys ***                                  128

CTTGCGGCCGCTGAT                                                              690
```

Fig. 5C

```
    GATCGTCGACCTCAAGGTCCTTACAATG AAA TGC AGC TGG GTC ATC TTC TTC CTG    55
                                 Met Lys Cys Ser Trp Val Ile Phe Phe Leu  10

ATG GCA GTG GTT ACA G GTAAGGAGCTCCCAAGTCCCAAACTTGAGGGGCCATACACTCTGT   116
Met Ala Val Val Thr G                                                   15

GACAGTGGCAGTCACTTTGCCTTTCTTTCTACAG GG GTC AAT TCA GAG GTT CAG CTG   173
                                       ly Val Asn Ser Glu Val Gln Leu    23

CAG CAG TCT GGG GCT GAG CTT GTG AGG CCA GGG GCC TTA GTC AAG TTG TCC   224
Gln Gln Ser Gly Ala Glu Leu Val Arg Pro Gly Ala Leu Val Lys Leu Ser    40

TGC AAA GCC TCT GGC TTC AAC ATT AAA GAC TAC TAT ATG TAC TGG GTA AAA   275
Cys Lys Ala Ser Gly Phe Asn Ile Lys Asp Tyr Tyr Met Tyr Trp Val Lys    57

CAG AGG CCT GAA CAG GGC CTG GAG TGG ATT CGA TGG ATT GAT CCT GAA AAT   326
Gln Arg Pro Glu Gln Gly Leu Glu Trp Ile Gly Trp Ile Asp Pro Glu Asn    74

GGT AAT ACT GTT TAT GAC CCG AAG TTC CAG GGC AAG GCC AGT ATA ACA GCA   377
Gly Asn Thr Val Tyr Asp Pro Lys Phe Gln Gly Lys Ala Ser Ile Thr Ala    91

GAC ACA TCC TCC AAC ACA GCC TAC CTG CAG CTC AGC AGC CTG GCA TCT GAG   428
Asp Thr Ser Ser Asn Thr Ala Tyr Leu Gln Leu Ser Ser Leu Ala Ser Glu   108

GAC ACT GCC GTC TAT TAC TGT GCT TAC TAC GGT ACT AGC TAC TGG TTT CCT   479
Asp Thr Ala Val Tyr Tyr Cys Ala Tyr Tyr Gly Thr Ser Tyr Trp Phe Pro   125

TAC TGG GGC CAA GGG ACT CTG GTC ACT GTC TCT GCA G GTGAGTCCTACCTTCTC   533
Tyr Trp Gly Gln Gly Thr Leu Val Thr Val Ser Ala                       137

CGCGGCCGCTGAT                                                         546
```

Fig. 5D

PCR primers for Vλ:

(a) 5'λ1: GATCGTCGACCITGGTTTGTGAATTATG
(a) 5'λ2: GATCGTCGACAGTAGTACCTGCATTATG
    3'λ1: GATCGCGGCCGCAAAGGAGGIAGGAGTIAC
    3'λ2: ATCAGCGGCCGCAAGAAGCATTAAAGCCAC
    3'λ3: ATCAGCGGCCGCAAGAAGCTTTGAAACTAC

Fig. 6A

PCR primers for Vκ:

(a) 5'κ1: GATCGTCGACAAATTCAAAG/TACAA/CAAT
(f) 5'κ2: GATCGTCGACAAGACTCAGCCTGACATG
(a) 5'κ3: GATCGTCGACAAGTTCAAAGACAAAATG
(d) 5'κ4: GATCGTCGACAGACTCAGCCTIGACATG
(h) 5'κ5: GATCGTCGACAGCAGGGGGAGCAGGATG
(b) 5'κ6: GATCGTCGACAGGGAAAGTTTGAAGATG
(d) 5'κ7: GATCGTCGACATACATCAGACCAGCATG
(d) 5'κ8: GATCGTCGACATCTAGC/TTCTCAGAGATG
(f) 5'κ9: GATCGTCGACATGCATCACACCAGCATG
(d) 5'κ10: GATCGTCGACCACCAAGTTCTCAGAATG
(h) 5'κ11: GATCGTCGACCAGAGCAGCAGGGACATG
(h) 5'κ12: GATCGTCGACCAGGGACAAGTGGGAATG
(e) 5'κ13: GATCGTCGACCATTCAGAACTCAGCATG
(h) 5'κ14: GATCGTCGACGCGAGTCAGACCAGCATG
(b) 5'κ15: GATCGTCGACGGACACAGTTTAGATATG
(i) 5'κ16: GATCGTCGACGGACTCAGCATGGACATG
(e) 5'κ17: GATCGTCGACGGAGACGTTGTAGAAATG
(f) 5'κ18: GATCGTCGACGGATACACCATCAGCATG
(i) 5'κ19: GATCGTCGACGGCAAA/GGGCATCAAGATG
(i) 5'κ20: GATCGTCGACGGCAGG/TGGA/GAGCAAGAT
(g) 5'κ21: GATCGTCGACGGTCACAGCACAAACATG
(g) 5'κ22: GATCGTCGACGGTTGCCTCCTCAAAATG
(b) 5'κ23: GATCGTCGACGTTCATTTCCTCAAAATG
(a) 5'κ24: GATCGTCGACTATCAAGTTCICAGAATG
(c) 5'κ25: GATCGTCGACTCTCAAGTTCTCAGAATG
(a) 5'κ26: GATCGTCGACTCTTGTGAATTAATCATG
(c) 5'κ27: GATCGTCGACTGAAAACACACAGACATG
(c) 5'κ28: GATCGTCGACTGATAAAGCCAAGGAATG
(e) 5'κ29: GATCGTCGACTGATCACACACAGA/TCATG
(g) 5'κ30: GATCGTCGACTTCCAGCTCTCAGAGATG
     3'κ1: ATCAGCGGCCGCAGAGAG/CTTTGGATTCTAC
     3'κ2: ATCAGCGGCCGCAAGAGTTGAGAAGACTAC
     3'κ3: ATCAGCGGCCGCAGTTGAGCAAAAATGTAC
     3'κ4: ATCAGCGGCCGCAAATGAGCAAAAA/GTCTAC
     3'κ5: ATCAGCGGCCGCAAGATGAGAAAAGTGTAC

Fig. 6B

PCR primers for VH:

(j) 5'H1: GATCGTCGACACACAGACTCACACCATG
(g) 5'H2: GATCGTCGACACACAGGACCTCACCATG
(j) 5'H3: GATCGTCGACACACAGGATCTCACCATG
(g) 5'H4: GATCGTCGACACACAGGGCATTGCCATG
(b) 5'H5: GATCGTCGACACACTGACTCAAAACATG
(c) 5'H6: GATCGTCGACACACTGACTCAAACCATG
(j) 5'H7: GATCGTCGACACACTGACTCACACCATG
(j) 5'H8: GATCGTCGACACACTGACTCCAACCATG
(c) 5'H9: GATCGTCGACACACTGACTCTAACCATG
(k) 5'H10: GATCGTCGACACACTGACTCTCACCATG
(c) 5'H11: GATCGTCGACACACTGACTTTCACCATG
(h) 5'H12: GATCGTCGACACATAGACTCTAACCATG
(b) 5'H13: GATCGTCGACACATTGACTCAAACCATG
(g) 5'H14: GATCGTCGACAGCCTCCATCAGAGCATG
(e) 5'H15: GATCGTCGACAGCCTCCGTCAGAGCATG
(a) 5'H16: GATCGTCGACATTATAACATTGAACATG
(b) 5'H17: GATCGTCGACCAAGTCTTAGACATCATG
(k) 5'H18: GATCGTCGACCACACATCCCTTACCATG
(h) 5'H19: GATCGTCGACCACAGACACCTCACCATG
(e) 5'H20: GATCGTCGACCACAGACCA/CCTCACCATG
(k) 5'H21: GATCGTCGACCACAGACCTGTCAACATG
(h) 5'H22: GATCGTCGACCACAGACCTGTCACCATG
(e) 5'H23: GATCGTCGACCACGGAACCCTCACCATG
(f) 5'H24: GATCGTCGACCACGGACCCCTCACCATG
(f) 5'H25: GATCGTCGACCACGGACCCCTCACGATG
(k) 5'H26: GATCGTCGACCACTCGACTCTAACCATG
(h) 5'H27: GATCGTCGACCACTGGTGTGCAGTCATG
(a) 5'H28: GATCGTCGACCACTTCTTAGACATCATG
(f) 5'H29: GATCGTCGACCAGAGTCCACTCA/GCCATG
(l) 5'H30: GATCGTCGACCCTGTCACTGACTTCATG
(c) 5'H31: GATCGTCGACCTCAAGGTCCTTACAATG
(l) 5'H31b: GATCGTCGACCTCCAGGTCCTTACAATG
(i) 5'H32: GATCGTCGACCTCAGTCCTGTCACCATG
(l) 5'H33: GATCGTCGACCTCAGTCCTGTCACTATG
(i) 5'H34: GATCGTCGACGCAGAGGACCTCACAATG
(d) 5'H35: GATCGTCGACGCCTTTACAGACTTCATG
(f) 5'H36: GATCGTCGACGGACCTCACCATGGGATG
(i) 5'H37: GATCGTCGACGGGTGTTGCCTAAGGATG
(d) 5'H38: GATCGTCGACGGTGTA/TGCCTAAAAGATG
(l) 5'H39: GATCGTCGACGGTGTTGCCTAAAGGATG
(a) 5'H40: GATCGTCGACGTTGTAGCCTAAAAGATG
(d) 5'H41: GATCGTCGACTCAGTCCTTGTCACTATG
3'H1: ATCAGCGGCCGCAAAGAAAAAGCCAGCTTAC
3'H2: ATCAGCGGCCGCGAGGTTT/GTAAGGACTCAC
3'H3a: ATCAGCGGCCGCGGAGAAA/GTTAGGACTCAC
3'H3b: ATCAGCGGCCGCGGAGAAGT/GTAGGACTCAC
3'H4: ATCAGCGGCCGCTGGAGAGGCCATTCTTAC

Fig. 6C

Jλ oligo probes:

Jλ1 : GTCAGTTTGGTTCCTCCAC
Jλ2 : GTGACCTTGGTTCCACCGC
Jλ3 : GTGACCTTGGTTCCACTGC
Jλ4 : GTCAATCTGGTTCCACCTC

Fig. 6D

Jκ oligo probes:

Jκ1 : GTGCCTCCACCGAACGTCC
Jκ2 : GTCCCCCTCCGAACGTGT
Jκ3 : GTCCCATCACTGAATGTGA
Jκ4 : GTCCCGAGCCGAACGTGA
Jκ5 : GTCCCAGCACCGAACGTGA

Fig. 6E

JH oligo probes:

JH1 : GACCGTGGTCCCTGCGCCC
JH2 : GAGAGTGGTGCCTTGGCCC
JH3 : GACCAGAGTCCCTTGGCCC
JH4 : GACTGAGGTTCCTTGACCC

Fig. 6F

PCR AMPLIFICATION OF REARRANGED GENOMIC VARIABLE REGIONS OF IMMUNOGLOBULIN GENES

BACKGROUND OF THE INVENTION

The development of mouse hybridoma technology has allowed the production of antibodies (Ab) specific for a wide range of antigens. Mouse monoclonal antibodies (mAb) have been used extensively for diagnosis and, in a few cases, for human therapy and in vivo diagnostics. Administration of murine antibodies to humans has been observed to induce a strong human anti-mouse antibody response (HAMA) after single or repeated treatments, thus precluding long-term treatment using these antibodies. Moreover, rodent antibodies are rapidly cleared from human serum and often do not interact effectively with the human immune system. Since human hybridomas are generally unstable and secrete low amounts of antibodies (frequently IgMs), considerable effort has been directed at rendering foreign antibodies (e.g., murine antibodies) more similar to those of the host to which they are administered (e.g., a human). Alternatives to human hybridoma-derived antibodies have been developed in which mouse immunoglobulin sequences (e.g., constant regions) are replaced with corresponding sequences derived from human immunoglobulin genes. Two examples of this type of antibody are (1) chimeric mAbs, in which murine variable regions are combined with human constant regions (Morrison et al., Proc. Natl. Acad. Sci. USA 81:6851–6855, 1984; Boulianne et al., Nature 312:643–30 646, 1984), and (2) humanized mAbs, in which murine CDRs (complementarity determining regions) replace the corresponding sequences in human ixmunoglobulins (Jones et al., Nature 321:522–525, 1986; Co et al., Nature 351:501–502, 1991). These engineered antibodies retain their target specificity and generally exhibit reduced HAMA responses when injected into patients. In addition, desired effector functions of antibodies for certain clinical applications can be obtained by using constant regions corresponding to the appropriate immunoglobulin isotype.

Despite these advances, cloning of variable region sequences has been a limiting step in the rapid construction of chimeric and isotype switched antibodies. Polymerase chain reaction (PCR) amplification of immunoglobulin heavy and light chain variable regions has facilitated this step. However, the high degree of DNA sequence polymorphism in leader and variable sequences of both heavy and light chain genes has required the preparation of complex sets of degenerate primers (Jones et al., Bio/Technology 9:88–89, 1991; Kettleborough et al., Eur. J. Immunol. 23:206–211, 1993; Le Boeuf et al., Gene 82:371–377, 1989; Orlandi et al., Proc. Natl. Acad. Sci. USA 86:3833–3837, 1989). In the case of 5' primers, these primers have usually been designed to correspond to the first framework of the variable region (FR1) and, in a few cases, to the leader peptide sequence (L). The 3' primers have usually been designed to correspond to the framework 4 (FR4) region, which displays limited polymorphism, or to the constant region, in which conserved, isotype-specific sequences are easily identified. Although complex sets of 5' and 3' primers have been designed, they do not always match the DNA template completely (Gavilondo-Cowley et al., Hybridoma 9:407–417, 1990; Leung et al., BioTechniques 15:286–292, 1993). Native sequences of the immunoglobulin heavy and light chain genes may therefore be altered in the FR1 and/or FR4 regions by the PCR amplification process. Modifications of the N-terminal region of an immunoglobulin, particularly the light chain variable region (VL), in which the amino acid at position two is part of the predicted canonical structure for CDR1 (Chothia et al., Nature 342:877–883, 1989), have been shown to drastically reduce the affinity of immunoglobulins for their antigens. Moreover, expression levels of the recombinant antibodies may also be altered when mutations occur in the leader peptide. In most studies involving PCR amplification of immunoglobulin H (heavy) and κ/λ (light) chain variable regions using these primers, cDNA templates were used, resulting in the generation of fragments containing incomplete VH and VL sequences, which may or may not be linked to part of the constant region.

SUMMARY OF THE INVENTION

We have designed a method for isolating nucleic acids encoding immunoglobulin Fv (variable) fragments from genomic DNA of hybridoma cells producing specific monoclonal antibodies. Specific primers corresponding to (1) the 5' untranslated region (UTR) of the variable region and (2) the intron downstream of the rearranged JH/Jκ/λ sequences are used in this method. The method can be used to amplify and clone genomic DNA corresponding to λ and κ light chain variable genes, as well as heavy chain variable genes. The variable genes isolated by this method can easily be inserted into expression vectors containing heterologous (e.g., human) light and heavy chain constant genes, thus facilitating isotype switching or antibody chimerization. Using this method, we have cloned for the first time genes encoding the variable regions (Fv) of the kappa light chain and heavy chain of the antibody produced by hybridoma cell line HNK-20.

Accordingly, in one aspect the invention features substantially pure DNA (genomic DNA or cDNA) encoding a variable region of the antibody produced by hybridoma cell line HNK-20. The variable region can be from the immunoglobulin heavy chain of the antibody, or from the immunoglobulin light chain of the antibody. The DNA may further encode an immunoglobulin constant region, such as a human immunoglobulin constant region. The immunoglobulin can be of any isotype, including, but not limited to an IgA (e.g., IgA1, IgA2, and sIgA), IgG, IgM, IgD, or IgE isotype. In the case of an IgA isotype, the immunoglobulin heavy chain can be an α chain.

In one embodiment, the substantially pure DNA contains the sequence of FIG. 5B, or degenerate variants thereof, and encodes the amino acid sequence of FIG. 5B. In another embodiment, the substantially pure DNA contains a sequence having about 50% or greater sequence identity to the DNA sequence of FIG. 5B. In another embodiment, the substantially pure DNA a) is capable of hybridizing to the DNA sequence of FIG. 5B under stringent conditions; and b) encodes a polypeptide having a biological activity of a HNK-20 variable region.

In another embodiment, the substantially pure DNA contains the sequence of FIG. SC, or degenerate variants thereof, and encodes the amino acid sequence of FIG. 5C. In another embodiment, the substantially pure DNA contains a sequence having about 50% or greater sequence identity to the DNA sequence of FIG. 5C. In another embodiment, the substantially pure DNA a) is capable of hybridizing to the DNA sequence of FIG. 5C under stringent conditions; and b) encodes a polypeptide having a biological activity of a HNK-20 variable region.

In another embodiment, the substantially pure DNA contains the sequence of FIG. 5D, or degenerate variants thereof, and encodes the amino acid sequence-of FIG. 5D. In another embodiment, the substantially pure DNA contains a sequence having about 50% or greater sequence identity to the DNA sequence of FIG. 5D. In another embodiment, the substantially pure DNA a) is capable of hybridizing to the DNA sequence of FIG. 5D under stringent conditions; and b) encodes a polypeptide having a biological activity of a HNK-20 variable region.

In another aspect of the invention, the DNA is operably linked to regulatory sequences, such as promoter and/or enhancer sequences, for expression of the variable region. In a related aspect, the invention features a vector (e.g., a plasmid or a viral vector) containing the DNA of the invention operably linked to a promoter sequence. The invention also features a cell (e.g., a myeloma cell) containing the DNA of the invention.

In another aspect, the invention features a recombinant antibody containing a variable region from the monoclonal antibody produced by hybridoma cell line HNK-20. In one embodiment, the variable region is from the immunoglobulin heavy chain of the monoclonal antibody. In another embodiment, the variable region is from the immunoglobulin light chain of the monoclonal antibody. The recombinant antibody may further contain a chimeric constant region, e.g., a human immunoglobulin constant region. The antibody of the invention may be of any immunoglobulin isotype, such as those listed above. Accordingly, the antibody of the invention may contain an a heavy chain, and thus be of the IgA isotype.

The invention also features a method of making a recombinant antibody containing a variable region from the monoclonal antibody produced by hybridoma cell line HNK-20. This method involves expression of DNA encoding the variable region of the antibody, as well as a constant region (e.g., a human constant region). Expression of the DNA may be carried out using any standard method known in the art. Preferably, the DNA is expressed in a cell, e.g., a myeloma cell. The cell is cultured under conditions in which the recombinant antibody is produced, and the antibody is subsequently purified from the cell or from the supernatant in which the cell was cultured, using standard methods.

In a final aspect, the invention features a method of isolating a nucleic acid containing a variable region of an immunoglobulin gene (e.g., the immunoglobulin gene is from hybridona cell line HNK-20). In this method, a first set of primers, each of which contains the sequence of a polymorphic variant of a segment of the 5' untranslated region of said immunoglobulin gene; and a second set of primers, each of which contains the sequence of a polymorphic variant of a segment of the intron 3' to the rearranged J region of said immunoglobulin gene; are used in a polymerase chain reaction containing genomic DNA that encodes the variable region of the immunoglobulin. A set of primers that contain sequences of the immunoglobulin gene is identified from the polymerase chain reaction, and subsequently is used to amplify the immunoglobulin gene.

By "promoter" is meant a minimal sequence element sufficient to direct transcription. Also included in the invention are those promoter elements which are sufficient to render promoter-dependent gene expression controllable for cell-type or tissue-specific expression, as well as elements which allow expression to be inducible by external signals or agents; such elements may be located in the 5' or 3' regions of, as well as within, the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 50 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705; Ausubel et al., eds. *Current Protocols in Molecular Biology*, Wiley & Sons, New York, 1989). Such software matches similar sequences by assigning degrees of homology to various substitutions, deletions, substitutions, and other modifications. Conservative substitutions for amino acids typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "substantially pure DNA" is meant DNA that is free of the genes which, in the naturally-occurring genome of the organism from which the DNA is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. "Stringent conditions", as used herein, are defined as follows. High stringency conditions include hybridization at about 42° C. in about 50% formamide; a first wash at about 65° C. in about 2×SSC and 1% SDS; followed by a second wash at about 65° C. in about 0.1% SSC. Lower stringency conditions for genes having about 50% sequence identity include hybridization at about 42° C. in the absence of formamide; a first wash at about 42° C. in about 6×SSC and about 1% SDS; followed by a second wash at about 50° C. in about 6×SSC and about 1% SDS.

Our method for isolating immunoglobulin variable region genes, using genomic DNA templates, does not lead to the production of fragments that need to be adapted for recombinant antibody expression, thus facilitating the generation of chimeric and isotype-switched immunoglobulins. Variable regions with intact coding sequences, including full length leader peptides, are obtained using this method without requiring previous DNA sequencing. Thus, isotype switched mouse Ig and chimeric mouse-human Ig can easily be produced. Chimeric antibodies containing constant regions derived from the host to which the antibody is to be administered (e.g., a human), are advantageous for use in therapeutics, because such chimeric antibodies are less likely than heterologous antibodies (e.g., murine antibodies) to lead to an adverse immune response, e.g., an HAMA response, in the patient.

Other features and advantages of the invention will be apparent from the following detailed description and from the claims.

DETAILED DESCRIPTION

The drawings are first described.

Figure 1B:
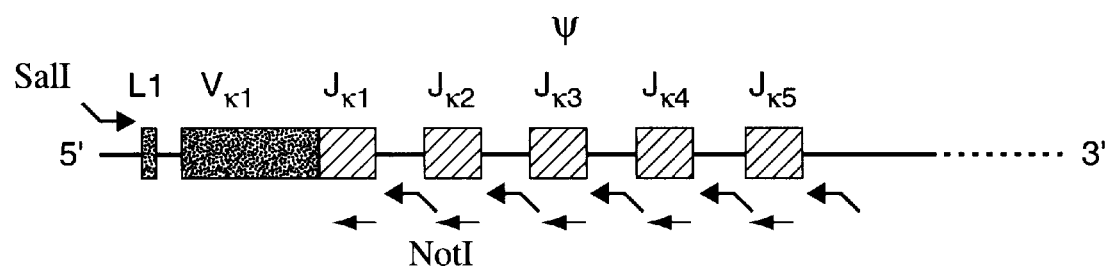
Figure 1C:
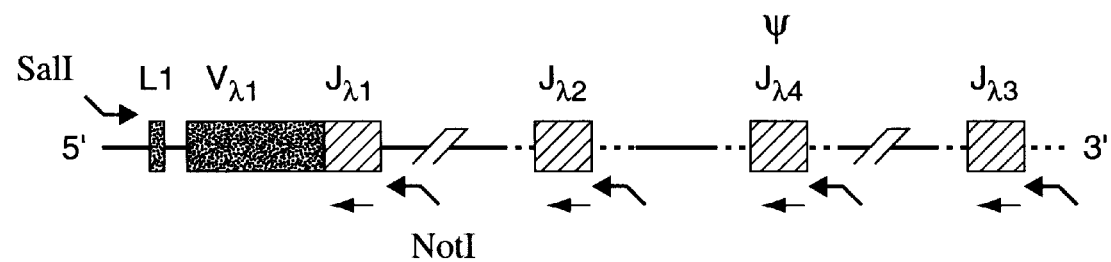

FIGS. 1A–1B are schematic representations of rearranged genes encoding the variable regions of heavy (FIG. 1A), kappa (FIG. 1B), and lambda (FIG. 1C) mouse immunoglobulin chains. Pseudogenes are indicated by "ψ"s. Bold arrows indicate PCR primers corresponding to the 5' untranslated region and the intron downstream of the rearranged J segment. SalI and NotI restriction sites have been added to the 5' ends of the PCR primers. Arrows below the J segments represent oligonucleotide probes used in Northern and Southern blot hybridization.

Figure 2A:
Figure 2B:
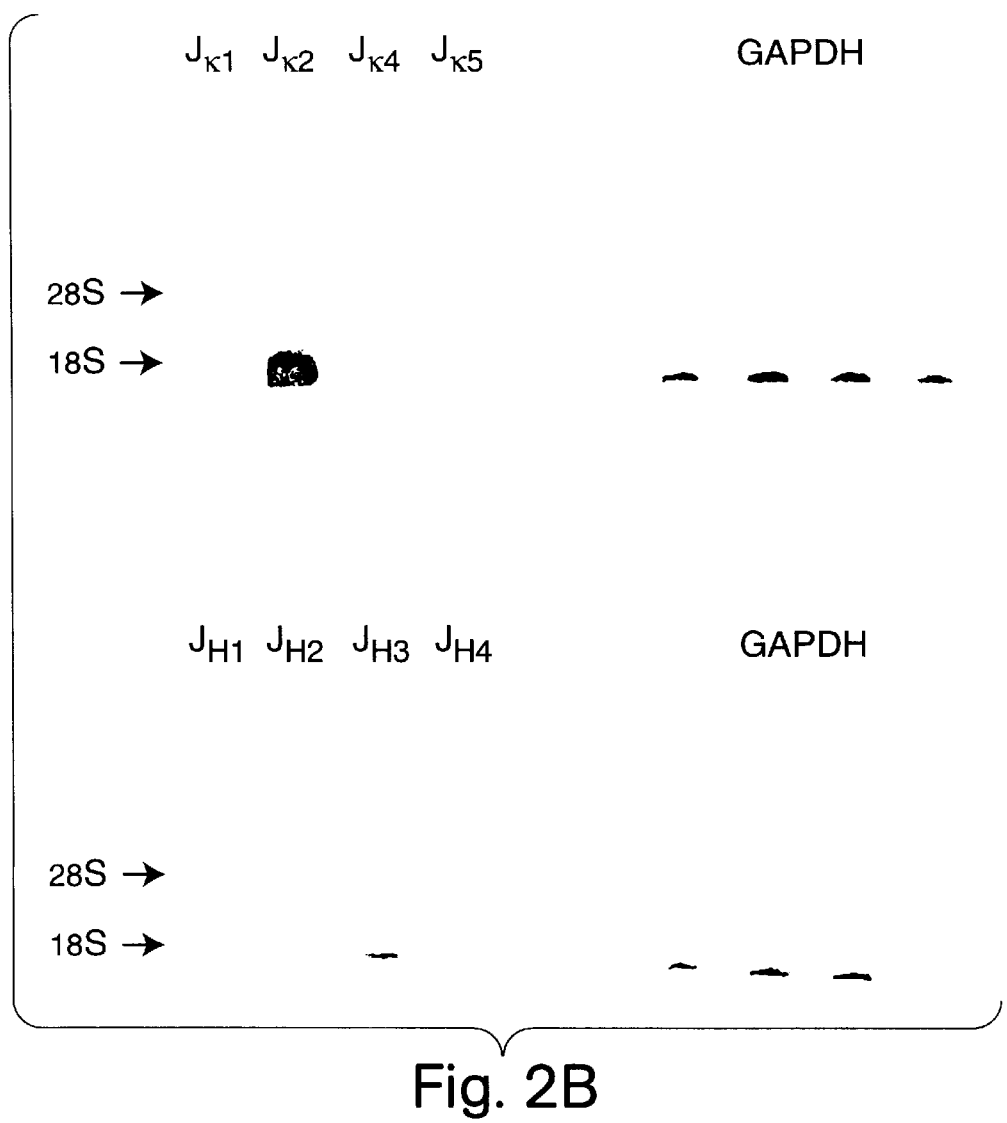
Figure 3A:
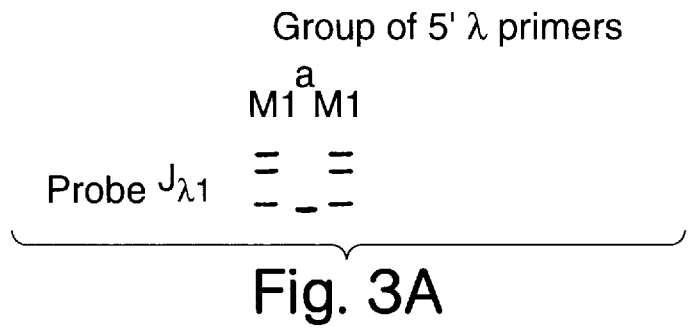
Figure 3B:
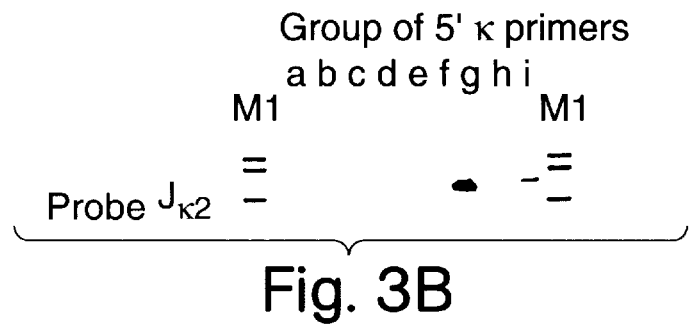
Figure 3C:
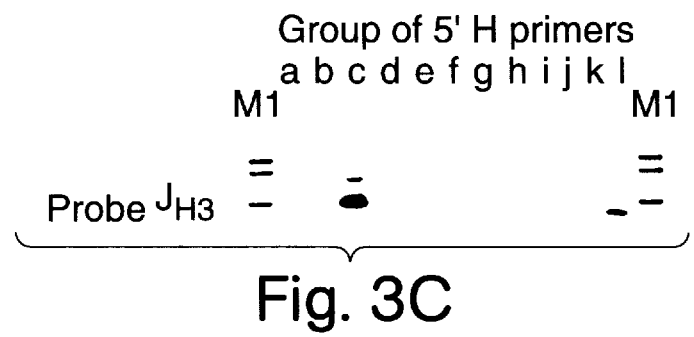
Figure 3D:
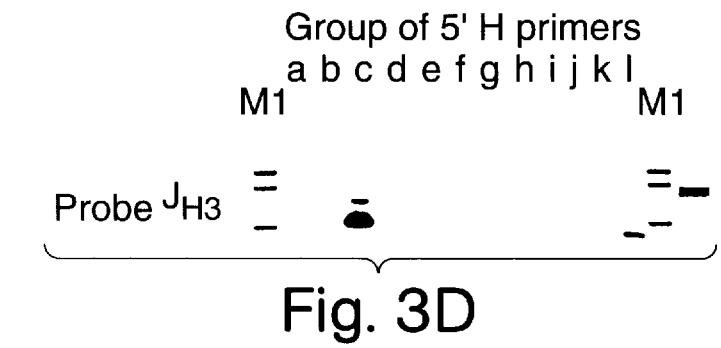
Figure 3E:
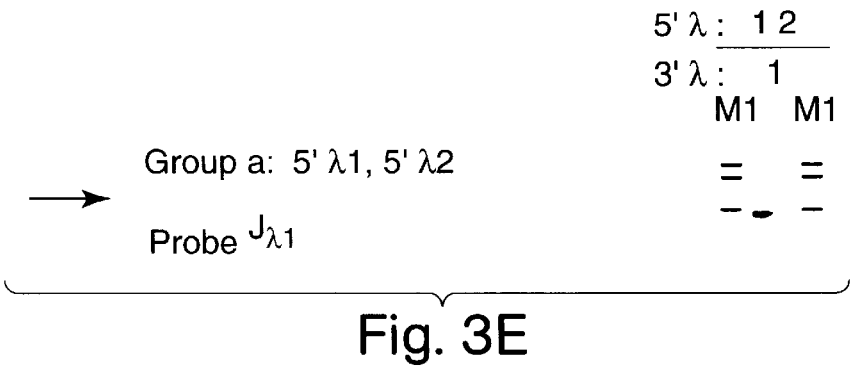
Figure 3F:
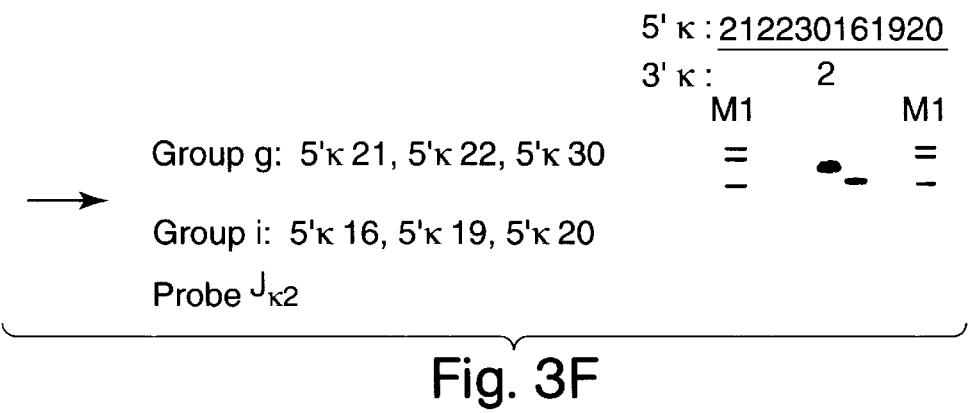
Figure 3G:
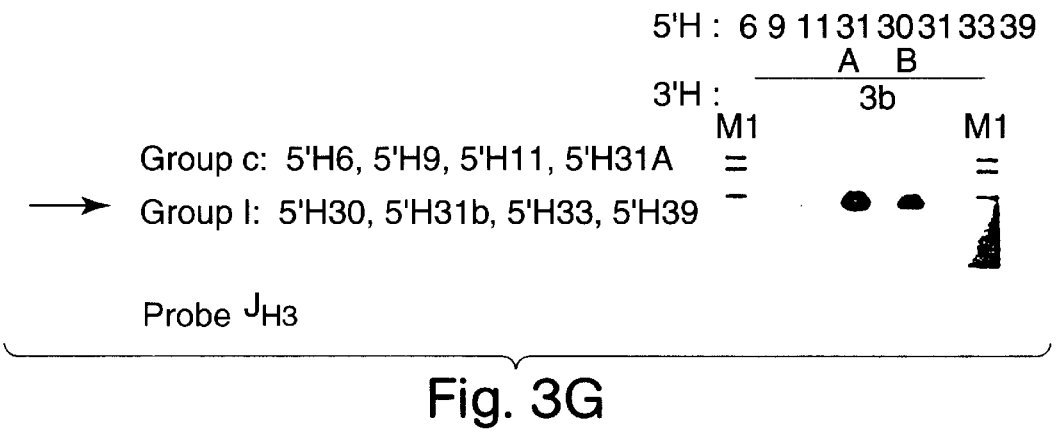

FIGS. 2A and 2B are Northern blots of RNA isolated from hybridoma cell lines 3G3 and HNK-20 probed with oligonucleotides homologous to the JH, Jκ, and Jλ segments. FIG. 2A: Total RNA (10 μg per slot) from hybridoma cell line 3G3 (IgM, λ) was hybridized with oligonucleotides Jλ1, Jλ2, and Jλ3, as indicated in the figure. FIG. 2B: Total RNA (10 μg per slot) from HNK-20 (IgA, κ) was hybridized with Jκ1, Jκ2, Jκ4, and Jκ5; and JH1, JH2, JH3, and JH4 (see FIG. 6 for the sequence of the oligonucleotide probes), as indicated. Oligonucleotides specific for the pseudogenes (Jκ3 and Jκ4) were not used in these experiments. As an internal control for total RNA loading, the blots were rehybridized with a full length glyceraldehyde-3-phosphate-dehydrogenase (GAPDH) cDNA probe (McMaster et al., Proc. Natl. Acad. Sci. USA 74:4835–4838, 1977). Migration positions of ribosomal RNA are indicated.

FIGS. 3A–3G are Southern blots of amplified 3G3 Vλ, HNK-20 Vκ, and HNK-20 VH genomic fragments, made by following a two step PCR amplification method. In the first step (FIGS. 3A–3D), PCR amplification was carried out using groups of 2, 3, or 4, 5' primers (see FIG. 6) and a single 3' primer. The 3' primer for Vλ was: 3'λ1, for Vκ: 3'κ2, and for VH: 3'H3a or 3'H3b. In the second step (FIGS. 3E–3G), PCR amplification was performed separately with each of the 5' primers from the positive groups from the first set of reactions (FIGS. 3A–3D), allowing identification of the 5' primer(s) that generate(s) the signal in each positive group. PCR amplification with 3'H3a was omitted in the second step since 3'H3b generates stronger signals. Positions of size markers of 564, 831, and 947 basepairs are indicated in the lane labelled M1.

Figure 4A:
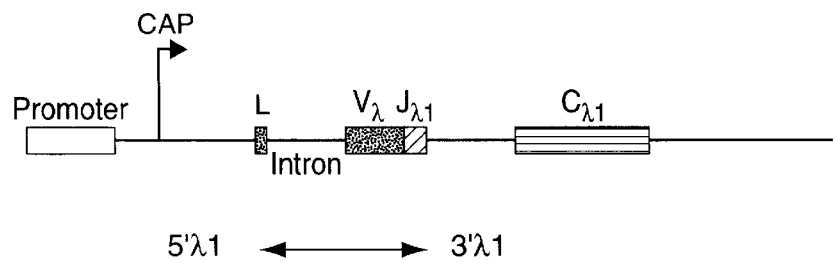
Figure 4B:
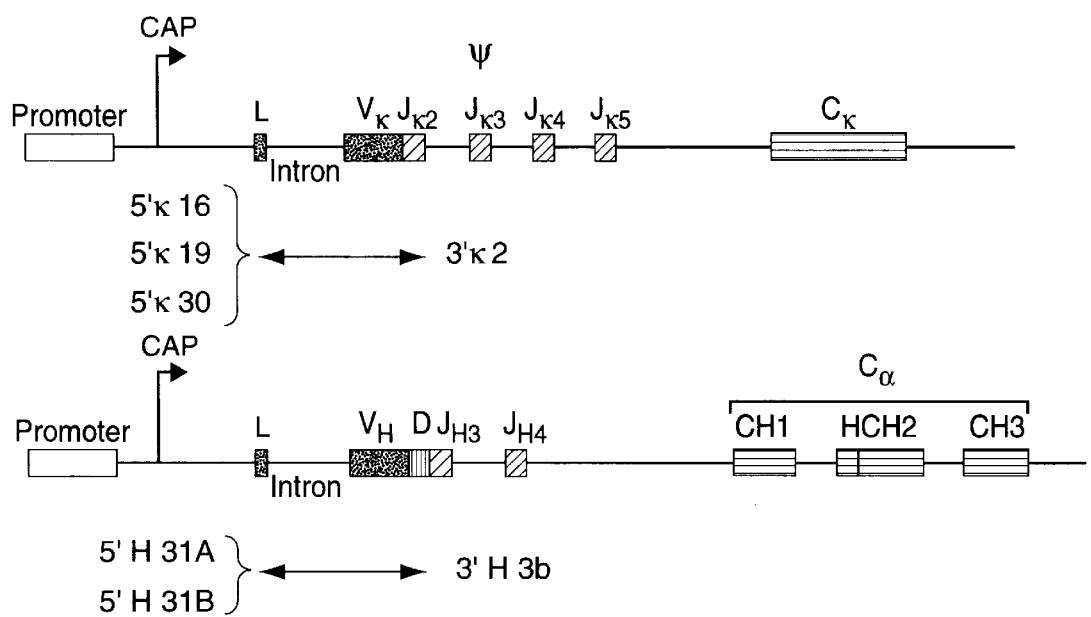

FIGS. 4A–4B are schematic representations of the rearranged 3G3 Vλ, HNK-20 Vκ, and VH regions. In FIG. 4A rearrangement of the lambda locus from 3G3 is shown. In FIG. 4B rearrangements of the kappa and heavy chain loci from HNK-20 are shown. Three different kappa chain gene rearrangements have been observed with the Jκ2 segment. For the heavy chain genes, 5'H31a and 5'H31b generate the same PCR product, hence a single rearrangement is observed for the heavy chain. The maps are not drawn to scale.

FIGS. 5A–5D are sequences of the PCR amplified 3G3 Vλ, HNK-20 Vλ, and HNK-20 VH regions. The sequences shown in FIGS. 5A, 5B, 5C, and 5D correspond to 3G3 Vλ (generated by 5'λ1-3'λ1), HNK-20 Vκ (generated by 5'κ16-3'κ2), HNK-20 VK (generated by 5'κ30-3'κ2), and HNK-20 VH (generated by 5'H31b-3'H3b), respectively. The sequences of the PCR primers are shown in bold, the CDR regions are underlined, and stop codons are indicated by stars. Regions homologous it to the Jλ, Jκ, and JH oligonucleotide probes are double underlined.

FIGS. 6A–6F are the nucleotide sequences of the PCR primers and probes used for the amplification of mouse Vλ, Vκ, and VH regions. SalI and NotI sites are in bold, and I represents inosine. Sequences are 5' to 3'. The names of the groups of 5' primers precede the numbering and sequences of the primers.

The Nonoclonal Antibody Produced by Hybridoma Cell Line HNK-20.

Respiratory Syncytial Virus (RSV) infection can lead to diseases of the upper or lower respiratory tract, including pneumonia and severe bronchiolitis (McIntosh et al., In B. NK Fields and D. M. Knipe (eds.), *Virology*, Raven Press, New York, pp. 1045–1072, 1990). HNK-20 is a murine hybridoma cell line that produces a monoclonal IgA antibody that recognizes the F glycoprotein of RSV. In addition to neutralizing RSV in plaque reduction assays, this antibody is effective at preventing and treating RSV infection when passively administered to mice intranasally.

Method for Isolating Immunoglobulin Variable Region Genes.

We have designed a strategy for the preparation of genomic fragments encoding the VH-D-JH (immunoglobulin heavy chain variable region) and VL-JL (immunoglobulin light chain variable region) regions of immunoglobulin genes. This strategy involves PCR amplification of genomic DNA prepared from hybridomas using specific primers corresponding to (1) the 5' untranslated region of the gene encoding the variable region, and (2) an intron downstream from specific rearranged JH/JL sequences. This method does not require previous knowledge of the sequence of any part of the gene encoding the target variable region, thus allowing rapid and efficient isolation of the genes.

Based on analysis of nucleotide sequence databases (e.g., the Genbank), sets of primers are designed corresponding to all of the sequences reported in the databases for a given organism (e.g., a mouse) for a specific region within the 5' UTR of the immunoglobulin variable region gene and for a specific region in the intron downstream of the rearranged J segment. In order to minimize the numbers of primers required to cover all of the possible known sequences for a given region (e.g., the 5' UTR), the most highly conserved specific regions within the region may be focused on. As a specific example, in the case of the 5' UTR of the murine variable heavy chain, 42 primers are required because of the relatively high degree of nucleotide sequence polymorphism (see below). In contrast, due to lower levels of sequence polymorphism, only 2 primers are required to cover all of the known possibilities for the 5' UTR of the murine immunoglobulin lambda variable region (see below). In a first set of PCR reactions, multiple primers covering all of the polymorphic sequences corresponding to the region the primers hybridize to can be used in a single reaction. In cases where a large number of primers are required, the primers can be divided up into several reactions based on, e.g., their melting temperatures. For example, for the 5' UTR of the murine heavy chain variable region, where 42 primers are required to cover all of the known polymorphic sequences, the reactions were divided up into 12 groups (see below). Primers contained in those reactions of the first set of PCR reactions folnd to be positive can subsequently be tested individually (i.e., in reactions containing only a single 5' primer and a single 3' primer) in order to identify the sets of primers that correspond to the sequence of the gene being amplified. These primers can then be used to prepare the fragment for cloning, in order to generate chimeric or isotype switched immunoglobulin genes. As no sequence information for the gene being amplified is required in the present method, isolating variable region genes from hybridoma cell lines is facilitated.

Variable regions isolated by this method can be fused to genes encoding heterologous constant regions in order to produce chimeric (e.g., a murine variable region fused to a human constant region) or isotype switched immunoglobulin genes, that can in turn be used to make chimeric or isotype switched antibodies. We have used this method to produce chimeric immunoglobulin genes, including one containing the HNK-20 heavy chain variable region fused to a human heavy chain constant region, and another containing the HNK-20 kappa light chain variable region fused to a human kappa light chain constant region. Co-expression of these genes leads to the production of recombinant antibodies having the specificity of the antibody produced by hybridoma cell line HNK-20, and the effector regions of a human antibody.

The recombinant antibodies of the invention can be used to prevent RSV infection, or to treat diseases caused by RSV infection (e.g., upper or lower respiratory tract infections, such as pneumonia or bronchiolitis). The recombinant antibodies of the invention may be administered to any hosts that are susceptible to RSV infection, including, but not limited to, humans (adults, children, and infants), chimpanzees, cattle, cebus monkeys, owl monkeys, ferrets, lambs, mice, rats, and cotton rats. The therapeutic compositions of the invention may be administered to a patient by any appropriate mode. Typically, the antibody is administered to a mucosal surface of the subject, for example, an oral or an intranasal surface. The antibodies of the invention can be administered in an amount determined to be effective for prevention or treatment of RSV infection by one skilled in the art. An appropriate dosage is one which effects a reduction in the disease caused by RSV infection, and/or one which is effective at preventing RSV infection. It is expected that the dosages will vary, depending upon the mode and route of administration; the age, weight, and health of the recipient; the nature and extent of the disease; the frequency and duration of the treatment; the type, if any, concurrent therapy; and the desired effect. For example, the amount of antibody administered may be in the range of 50 $\mu$g/kg to 5 mg/kg body weight. The invention also includes compositions containing the antibodies of the invention in a pharmaceutically acceptable carrier and/or diluent, e.g., saline. Suitable pharmaceutical carriers, as well as pharmaceutical necessities for use in pharmaceutical formulations, are described in Remington's Pharmaceutical Sciences, a standard reference text in this field, and in the USP/NF.

The antibodies of the invention may also be used in diagnostic methods for identifying patients infected with RSV, using any of a number of standard assay systems that are well known in the art. Such assay systems include, but are not limited to, enzyme linked immunosorbent assays (ELISA), solid phase radiometric assays, immunofluorescent microscopy, and immunoelectron microscopy (see, e.g., Coligan et al., eds., *Current Protocols in Immunology*, John Wiley & Sons, New York, 1992). In these methods, an antigen (e.g., from a biological sample, such as cellular material or secretions) is contacted with an antibody of the invention, and specific binding of the antigen and the antibody is detected as a measure of the presence of the antigen in the sample. The detection can be facilitated by the presence of labels on the antibodies of the invention or labels on secondary antibodies that recognize the antibodies of the invention. The labels that can be employed in these assays include, but are not limited to, radio-labels, enzyme labels (e.g., horse-radish peroxidase), biotin-labels, and chemiluminescent labels, and are detected using standard methods.

Genes encoding immunoglobulin variable regions (both light (kappa and lambda) and heavy chains) isolated using the methods of the present invention can be fused to genes encoding immunoglobulin constant regions (e.g., human constant region genes) in order to make genes encoding chimeric or isotype switched recombinant antibodies (see, e.g., U.S. Pat. No. 4,816,397, issued Mar. 28, 1989; hereby incorporated by reference; and Morrison et al., Proc. Natl. Acad. Sci. USA 81:6851–6855, 1984; hereby incorporated by reference). For example, in order to generate an IgA antibody, the variable region can be fused to an a constant region. Different types of constant regions that can be used to make the chimeric antibodies of the invention are well known in the art (see, e.g., Roitt et al., eds. *Immunology*, Gower Medical Publishing, London, 1989), and can be isolated and cloned to make the chimeric and/or isotype switched genes of the invention using standard methods (see, e.g., Sambrook et al., eds. *Molecular Cloning: A Laboratory Manual*, Cold Spring Harbor Laboratory Press, Cold Spring Harbor, New York, 1989; and Coligan et al., supra). In order to facilitate cloning of the variable genes into vectors, preferably, the PCR primers used in their amplification contain in their 5' ends sequences recognized by restriction endonucleases. Vectors into which the variable region genes and chimeric genes of the invention can be cloned include both plasmid and viral vectors. Preferred vectors for use in the invention are expression vectors containing appropriate heterologous heavy or light chain constant genes. For example, genes encoding kappa light chain and heavy chain variable regions can be cloned into plasmids such as pUHW$\kappa$ and pUHW$\gamma$1, respectively (Weissenhorn et al., Gene 106:273–277, 1991, hereby incorporated by reference). These plasmids contain a combination of a heavy-chain enhancer and a $\mu$-gene promoter, as well as a polylinker into which genes encoding variable regions can be inserted. Another vector that can be used in the invention is the pING expression vector (Chomczynski et al., Biochem. Biophys. Res. Commun. 122:340–344, 1984, see below).

The genes of the invention are cloned into the vectors so that the genes are operably linked to appropriate promoter/enhancer sequences. Any promoter that is capable of directing initiation of transcription in a eukaryotic cell may be used in the invention. For example, non-tissue specific promoters, such as the cytomegalovirus (DeBernardi et al., Proc. Natl. Acad. Sci. USA 88:9257–9261, 1991, and references therein), mouse metallothionine I gene (Hammer et al., J. Mol. Appl. Gen. 1:273–288, 1982), HSV thymidine kinase (McKnight, Cell 31:355–365, 1982), and SV40 early (Benoist et al., Nature 290:304–310, 1981) promoters may be used. Preferred promoters for use in the invention include those which direct expression in myeloma cells, as are described above.

Expression of the genes encoding the chimeric and/or isotype switched antibodies of the invention can be achieved using any of a number of methods standard in the art. For example, vectors, e.g., plasmids, containing the HNK-20 variable region(s) fused to heterologous constant regions can be transfected into a cell in which the gene is expressed, either constitutively or upon induction. The genes can be transfected into the cells using any standard method in the art, including, but not limited to, electroporation, calcium phosphate precipitation, protoplast fusion, and the use of viral vectors or lipids that are coupled with the genes (see, e.g., Sambrook et al., supra). Any cell in which the genes of the invention can be expressed to produce the antibodies of the invention may be used. Such cells include, but are not limited to, myeloma cells, such as non-Ig-producing myeloma cells. As a specific example, Sp2/0-Agl4 cells, which are murine myeloma cells that do not secrete or synthesize any immunoglobulin chains, can be used. Sp2/0-Agl4 cells can be obtained from the American Type Culture Collection, 12301 Parklawn Drive, Rockville, Md. 20852-1776, and have been designated ATCC CRL 1581 (see also Ochi et al., Proc. Natl. Acad. Sci. USA 80:6351–6355, 1983). Other cell lines that can be used in the invention include P3X63Ag8.653 (ATCC CRL 1580) and Sp2/01-Ag (ATCC CRL 8006).

The antibodies of the invention can be produced by culturing cells expressing the genes encoding them using standard methods. The antibodies are then purified from the cells and/or cell culture supernatants using standard methods (see, e.g., Coligan et al., supra). The culture conditions may be scaled-up using standard methods, in order to generate large quantities of antibody. In addition, the antibodies may be purified from ascites using standard methods.

Experimental Results

Design of the Primers and Probes for PCR Amplification of Mouse VH and VL Genes.

Most strategies used to amplify mouse VH and VL genes generate fragments encoding variable regions that are either truncated or contain mutations in their 5' and/or 3' ends. We have developed a PCR method for amplifying Fv (variable) genes that results in preservation of the entire Fv sequence. The primers used in this method hybridize to the 5' untranslated region (the 5' primers) and in the intron downstream of the rearranged J segment of the lambda, kappa, and heavy chain genes (the 3' primers; FIG. 1).

DNA sequence comparisons of 5' untranslated regions and introns downstream from J segments were performed using data from Kabat (Kabat et al., *Sequences of Proteins of Immunological Interest,* 5th Ed., U.S. Dept. Health and Human Services, Washington, D.C., 1991) and the Genbank and European Molecular Biology Laboratory (EMBL) libraries, and were further analyzed with the Genetics Computer Group (GCG, Madison, Wis.) package programs. Alignment of the DNA sequences of the 5' untranslated region revealed that the polymorphism in this region is globally identical to that of the leader paptide sequences. However, a stretch of around 20 nucleotides immediately upstream of the start codon (ATG) was observed to be more conserved throughout the alignment. We therefore designed a series of 5' PCR primers (18-mers) that terminate with the ATG sequence, ensuring perfect matches of the 3' ends of each primer with the template, as is critical for initiation of consistent priming by Taq polymerase. A SalI restriction site and 4 additional nucleotides, which facilitate digestion by the restriction endonuclease, were added to the 5' end of the primers in order to expedite cloning of the PCR fragments. Complex sets of 5' primers were synthesized consisting of 2 primers for lambda, 30 primers for kappa, and 42 primers for the heavy chain genes, some of which primers contained inosine residues, or were degenerate (FIG. 6).

In contrast, alignment of the 5' end of the intron sequences downstream from the J segments did not reveal significant polymorphism, so that 3' PCR primers specific for each of the Jλ, Jκ, and JH segments were designed in this intronic region. Single PCR primers were prepared corresponding to the regions downstream from each J segment, except for the JH3 segment, for which 2 primers were needed because of DNA sequence polymorphism. The 3' PCR primers are 18-mers, except for the primer downstream of the JH1 segment which was designed as a 20-mer because of the high A/T content of this region. A NotI restriction site and 4 additional nucleotides were added to the 5' end of these oligonucleotides in order to allow directional cloning of the PCR fragments into expression vectors (FIG. 6).

In order to ensure specificity of the PCR amplifications and to better characterize the VH-D-JH and VL-JL rearrangements, JL and JH-specific oligonucleotide probes were designed. Sets of oligonucleotides (19-mers) specific for each of the Jλ, Jκ, and JH segments, which exhibit very low polymorphism, were synthesized. These oligonucleotides were used as probes in both Southern blot analysis of the PCR fragments, and Northern blot analysis of total RNA extracted from mouse hybridoma cells.

Specificity of the Oligonucleotide Probes.

The specificity of the oligonucleotide probes homologous to each J segment in DNA—DNA hybridization was demonstrated by Southern blot hybridization using a variety of cloned VL and VH PCR fragments of known sequences. The specificity of these probes was also tested by hybridization to RNA on Northern blots. RNA from the hybridoma cells 3G3 (IgM, λ) and HNK-20 (IgA, κ) were hybridized with the Jλ, Jκ, and JH oligonucleotides (FIG. 2). The Northern blot analysis revealed that probes Jλ1, Jκ2, and JH3 generate signals at the expected sizes for 3G3 and HNK-20, respectively. Hybridization of HNK-20 RNA with the Jκ2 probe generated a much stronger signal than the JH3 probe, although these two probes had similar specific activities and identical calculated melting temperatures. This observation suggests either that the kappa chain transcript is much more abundant, or that several kappa chain transcripts hybridize with the Jκ2 probe. PCR amplification of the Vκ region supports the hypothesis that there are several different kappa chain gene rearrangements, one of which was derived from a transcribed pseudogene rearranged with the Jκ2 segment present in the immortalized fusion partner X63Ag8.653 (Strohal et al., Nucleic Acids Res. 15:2771, 1987; Carroll et al., Mol. Immunol. 25:991–995, 1988). Thus, at least one kappa pseudogene and one kappa functional gene transcript, both rearranged with the Jκ2 segment, are contributing to the strong signal observed. The Northern blots were then rehybridized with a probe specific for the house-keeping enzyme gene glyceraldehyde-3-phosphate-dehydrogenase (Piechaczyk et al., Nucleic Acids Res. 12:6951–6963, 1984) to control for the amount of RNA loaded (FIG. 2).

Use of the above-described J-specific oligonucleotide probes allows rapid characterization of the PCR products and immunoglobulin gene transcripts, and further allows identification of the J segment used in the rearrangement of the light and heavy chain genes.

Amplification and Detection of nAb Variable Region Genes.

Several immunoglobulin variable region genes have been amplified by PCR using genomic DNA prepared from mouse hybridoma cells. As specific examples, amplification of the Vλ gene of the hybridoma cell line 3G3, and the Vκ gene and VH genes of hybridoma cell line HNK-20 are described.

Based on the Northern blot analysis shown in FIG. 2, it was established that the λ chain gene was rearranged with Jλ1, the κ chain gene was rearranged with Jκ2, and the heavy chain gene was rearranged with JH3. Therefore, the 3' primers required for amplification were 3'λ1, 3'κ2, and 3'H3a/3'H3b. Due to the high level of polymorphism in the 5' untranslated region, if all of the 5' primers were used in separate PCR reactions, there would be 2 PCR reactions for lambda, 30 PCR reactions for kappa, and 42 PCR reactions for the heavy chain genes. To reduce this complexity, the 5' primers were divided into small groups of 2, 3, or 4 primers based on their melting temperatures (FIG. 6). One group was required for λ, 9 for κ, and 12 for the heavy chain gene primers, reducing the number of reactions to 1, 9, and 12, respectively.

The fragments produced in the first set of PCR amplification reactions, as analyzed on Southern blots hybridized with the Jλ1, Jκ2, and JH3 probes, corresponded to the expected sizes in the 5'λ group a, in the 5'κ groups g and i, and in the 5'H groups c and 1 (FIGS. 3A, 3B, 3C, and 3D). In the second set of PCR reactions, each 5' primer from the positive groups identified in the first set of PCR reactions was combined with the corresponding 3' primer, and the amplified fragments were analyzed on Southern blots using the Jλ1, Jκ2, and JH3 oligonucleotide probes. This experiment revealed that 5'λ1, 5'κ30, 5'κ16, 5'κ19 and 5'H31B generate the predicted signals (FIGS. 3E, 3F, and 3G), indicating that rearranged fragments were found for one lambda chain gene in 3G3, 3 kappa chain genes in HNK-20, and one heavy chain gene in HNK-20 (FIG. 4). Using another mouse hybridoma cell (PCG-4), secreting IgG2a with a κ chain, 3 different rearrangements of the kappa chain genes, and a single rearrangement of the heavy chain gene, were observed using the same PCR strategy. This observation is consistent with the presence of both a functional Vκ and aberrant Vκ transcripts in hybridoma cells obtained by fusion using cell lines derived from the original MOPC-21 tumor (Strohal et al., Nucleic Acids Res. 15:2771, 1987; Carroll et al., Mol. Immunol. 25:991–995, 1988). A third non-transcribed kappa chain rearrangement was detected in both HNK-20 and PCG-4 hybridomas which involved different Jκ segments. Since the only κ-chain gene that the fusion partner can Contribute is the non-functional NOPC-21 κ gene (Storb et al., Nucleic Acids Res. 8:4681–4687, 1980), this third rearrangement probably originated from the mouse B-cell that served as a fusion partner.

Sequence Analysis of the Vλ, Vκ, and VH PCR Fragments.

The PCR amplified variable regions of 3G3 Vλ, HNK-20 Vκ, the HNK-20 Vκ pseudogene, and HNK-20 VH were each cloned into the pING expression vector (Chomczynski et al., supra) and sequenced using the dideoxy chain termination method (Piechaczyk et al., Nucleic Acids Res. 12:6951–6963, 1984). The corresponding sequences are shown in FIGS. 5A–5D. The deduced amino acid sequences of the Vλ, Vκ, and VH fragments correspond to open reading frames consistent with those reported in the various gene banks. In all three PCR amplified fragments, the positions of the cysteines involved in intramolecular disulfide bridge formation were conserved. The presence of conserved stretches of amino acids corresponding to framework sequences allowed positioning of the CDRs (FIG. 5). Taken together, these observed structural features indicate that the amplified and cloned Fv fragments are functional and thus are able to recognize their corresponding antigen, provided they are expressed in appropriate host cells. Accordingly, the murine κ and H Fv genes corresponding to the antibody produced by the HNK-20 hybridoma have been inserted into expression vectors containing human heavy and light chain constant genes and transfected into myeloma cells.

Materials and Methods

Sources of DNA and RNA.

Mouse hybridoma cell line 3G3 (IgM, λ) was deposited with the American Type Culture Collection, and was assigned ATCC No. HB 8516. Mouse hybridoma cell line HNK-20 (IgA, κ), from OraVax Inc., Cambridge, USA, was deposited with the American Type Culture Collection (ATCC, Rockville, Md.) under the provisions of the Budapest Treaty on Jul. 1, 1993, and was assigned ATCC No. HB 11394. Genomic DNA was prepared as described (Gross-Bellard et al., Eur. J. Biochem. 36:32–38, 1973, hereby incorporated by reference). Total RNA was prepared from frozen cell pellets according to the guanidine/cesium chloride method (Glisin et al., Biochemistry 13:2633–2637, 1974; Chirgwin et al., Biochemistry 18:5294–5299, 1979).

Synthesis of Oligonucleotide Primers and Probes.

Oligonucleotides were synthesized using standard methods involving the μ-cyanoethyl phosphoramidite method and reverse phase HPLC purification (MWG-Biotech, Ebersberg, Germany).

DNA Amplification by PCR.

In vitro DNA amplification (PCR) was performed in a final volume of 100 μl volume using the thermal cycler 9600 from Perkin Elmer (Norwalk, Conn.). Reagents were added to the reaction to yield the following final composition: 10 mM Tris-HCl pH 8.3 (at 25° C.), 50 mM KCl, 2.5 MM $MgCl_2$, 0.001% gelatin (Sigma, Cat. No. G2500, St. Louis, Mo.), 200 μM dNTPs, 150 nM of each amplification primer, 1 μg of genomic DNA, and 2.5 units of AmpliTaq DNA polymerase (Perkin Elmer, Norwalk, Conn.). The cycling profile used is as follows: 5 minutes at 94° C.; 3 cycles of 1 minute at 94° C., 1 minute at 50° C., and 1 minute at 72° C.; 27 cycles of 1 minute at 94° C., 1 minute at 62° C., 1 minute at 72° C.; and a final incubation at 72° C. for 10 minutes.

Northern and Southern Blot Analysis.

Total RNA (10 μg) was denatured with glyoxal and fractionated by electrophoresis on an agarose gel (McMaster et al., Proc. Natl. Acad. Sci. USA 74:4835–4838, 1977). Transfer of RNA onto Gene Screen Plus membrane (Dupont, Wilmington, DE) was carried out according to the procedure described by the manufacturer. PCR products and genomic DNA prepared from hybridoma cells were fractionated on agarose gels and transferred onto Gene Screen Plus membrane as described (Chomczynski et al., Biochem. Biophys. Res. Commun. 122:340–344, 1984).

Northern and Southern blots were hybridized in identical conditions with $^{32}$P-labeled oligonucleotide probes specific for each of the Jλ, Jκ, and JH segments. The temperatures used for prehybridization and hybridization were TM-4° C., while the temperatures used for washing were TM-2° C. The melting temperatures (TMs) of the oligonucleotides were estimated by the formula: TM=4(G+C)+2(A+T). The TMs of the J-specific oligonucleotide probes are as follows: Jλ1=58° C., Jλ2=62° C., Jλ3=60° C., Jλ4=58° C., Jκ1=64° C., Jκ2=64° C., Jκ3=56° C., Jκ4=64° C., Jκ5=62° C., JH1=68° C., JH2=64° C., JH3=64° C., and JH4=60° C. For both Southern and Northern blots probed with oligonucleotide probes, the following conditions were used. Prehybridization was carried out for 3–4 hours in 2×SSC, 5×Denhardts, 0.1% SDS, and 5 mM EDTA. Hybridization was carried out for 14–18 hours in 5×SSC, 10×Denhardts, 20 mM sodium phosphate buffer (pH 7.0), 7% SDS, 100 μg/ml denatured herring sperm DNA, and $^{32}$P-labeled oligonucleotide (106 cpm/ml). After hybridization, the membranes were washed twice for 30 minutes in 3×SSC, 10×Denhardts, 5% SDS, and 70 am sodium phosphate buffer (pH 7.0); and twice for 30 minutes in 1×SSC and 1% SDS.

As an internal control for total RNA loading, Northern blots were hybridized with a glyceraldehyde-3-phosphate-dehydrogenase cDNA probe (Piechaczyk et al., Nucleic Acids Res. 12:6951–6963, 1984). For both Northern and Southern blots probed with the cDNA probe, the following conditions were used. Prehybridization was carried out for 3–5 hours at 42° C. in 50% deionized formamide, 5×Denhardts, 5×SSPE (30×SSPE=4.5 M NaCl, 0.3 M $NaH_2PO_4$, 30 mM EDTA, pH 7.7), 1% SDS, and 200 μg/ml denatured salmon sperm DNA. Hybridization was carried out for 14–18 hours at 42° C. in the same buffer including $^{32}$P-labeled cDNA probe (106 cpm/ml). After hybridization, the membranes were washed twice for 5 minutes in 2×SSPE at room temperature, once for 15 minutes in 2×SSPE and 0.5% SDS at 65° C., and once for 15 minutes in 0.5×SSPE at 65° C.

DNA Sequencing.

DNA sequences were determined by subcloning the L-VH-D-JH and L-VL-JL PCR fragments in the expression vector pING (Liu et-al., Gene 54:33–40, 1987), followed by sequencing using the dideoxy chain termination method (Sanger et al., Proc. Natl. Acad. Sci. USA 74:5463–5467, 1977).

Other Embodiments

The invention also includes any biologically active fragment or analog of the genes and antibodies of the invention. By "biologically active" is meant possessing any activity which is characteristic of HNK-20 variable genes or chimeric antibodies containing them. The invention also includes analogs of the HNK-20 immunoglobulin variable chains. Preferred analogs include those with sequences which differ from the sequences shown in FIGS. 5B–5D only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the immunoglobulin's biological activity. Analogs of the invention will generally exhibit at least 70%, preferably 80%, more preferably 90%, and most preferably 95%, or even 99%, homology with a segment of 20 amino acid residues, preferably 40 amino acid residues, or more preferably the entire sequence of an immunoglobulin of the invention. Alterations in the primary sequence include genetic variants, both natural or induced. Also included are analogs that include residues other than naturally occurring or synthetic amino acids, e.g., β or γ amino acids. Also included are immunoglobulins modified by in vivo chemical derivitization, including acetylation, methylation, phosphorylation, carboxylation, or glycosylation.

In addition to substantially full-length polypeptides, the invention also includes biologically active fragments of the immunoglobulins, which can be made using standard methods in the art. As used herein, the term "fragment," as applied to a polypeptide, such as an immunoglobulin, will ordinarily be at least 20 residues, more preferably at least 40 residues in length. Similarly, the invention also includes fragments of the genes encoding the immunoglobulins of the invention.

It is understood that the examples and embodiments described herein are for illustrative purposes only and that various modifications or changes in light thereof will be suggested to persons skilled in the art and are to be included within the spirit and scope of this application and the appended claims.

Other embodiments are within the following claims.

What is claimed is:

1. Substantially pure DNA comprising the sequence of SEQ ID NO:3, or degenerate variants thereof, and encoding the amino acid sequence of SEQ ID NO:4.

2. Substantially pure DNA comprising the sequence of SEQ ID NO:5, or degenerate variants thereof, and encoding the amino acid sequence of SEQ ID NO:6.

3. Substantially pure DNA comprising the sequence of SEQ ID NO:7, or degenerate variants thereof, and encoding the amino acid sequence of SEQ ID NO:8.

4. A method of isolating a nucleic acid comprising a variable region of an immunoglobulin gene from an organism, said method comprising the steps of:
   a. providing genomic DNA from said organism, wherein said genomic DNA comprises said variable region;
   b. providing a first set of primers, each of which contains the sequence of a polymorphic variant of a segment of the 5' untranslated region of an immunoglobulin gene from said organism;
   c. providing a second set of primers, each of which contains the sequence of a polymorphic variant of a segment of the intron 3' to the rearranged J region of an immunoglobulin gene from said organism;
   d. carrying out a polymerase chain reaction with said genomic DNA and said first and said second sets of primers;
   e. identifying a set of primers from said polymerase chain reaction that comprise sequences of said nucleic acid; and
   f. amplifying said nucleic acid with said identified set of primers.

5. The method of claim 4, wherein said immunoglobulin gene is from hybridoma cell line HNK-20.

* * * * *

UNITED STATES PATENT AND TRADEMARK OFFICE
CERTIFICATE OF CORRECTION

PATENT NO. : 6,258,529 B1
DATED : July 10, 2001
INVENTOR(S) : Jose Berdoz and Jean-Pierre Kraehenbuhl It is certified that error appears in the above-identified patent and that said Letters Patent is hereby corrected as shown below:

Column 1,
Line 29, "Nature 312:643-30 646," should be -- Nature 312:643-646, --
Line 32, "ixmunoglobulins" should be -- immunoglobulins --

Column 2,
Line 56, "FIG. SC," should be -- FIG. 5C, --
Line 67, "sequence-of" should be -- sequence of --

Column 3,
Line 26, "contain an a heavy" should be -- contain an α heavy --
Line 43, "hybridona" should be -- hybridoma --

Column 4,
Line 38, start a new paragraph after "sequence."

Column 5,
Line 59, "HNK-20 VK" should be -- HNK-20 $V_K$ --
Line 63, "homologous it to" should be -- homologous to --

Column 6,
Line 58, "folnd" should be -- found --

Column 8,
Line 9, "to an a constant" should be -- to an α constant --

Column 9,
Line 39, "paptide" should be -- peptide --

Column 10,
Line 46, "nAb" should be -- mAb --

UNITED STATES PATENT AND TRADEMARK OFFICE
CERTIFICATE OF CORRECTION

PATENT NO. : 6,258,529 B1
DATED : July 10, 2001
INVENTOR(S) : Jose Berdoz and Jean-Pierre Kraehenbuhl It is certified that error appears in the above-identified patent and that said Letters Patent is hereby corrected as shown below:

<u>Column 11,</u>
Line 28, "Contribute" should be -- contribute --
Lines 28-29, "NOPC-21" should be -- MOPC-21 --

<u>Column 12,</u>
Line 6, "µ-cyanoethyl" should be -- β-cyanoethyl --
Line 14, "2.5 MM" should be -- 2.5 mM --
Line 55, "70 am" should be -- 70 mM --

Signed and Sealed this

Twenty-second Day of October, 2002

*Attest:*

JAMES E. ROGAN
*Attesting Officer*     Director of the United States Patent and Trademark Office

SEQUENCE LISTING (1) GENERAL INFORMATION:

(iii) NUMBER OF SEQUENCES: 108

(2) INFORMATION FOR SEQ ID NO: 1:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:

```
GATCGTCGAC CGTGGTTTGT GAATTATGGC CTGGATTTCA CTTATACTCT CTCTCCTGGC      60

TCTCAGCTCA GGTCAGCAGC CTTTCTACAC TGCAGTGGGT ATGCAACAAT GCGCATCTTG     120

TCTCTGATTT GCTACTGATG ACTGGATTTC TCATCTGTTT GCAGGGGCCA TTTCCCAGGC     180

TGTTGTGACT CAGGAATCTG CACTCACCAC ATCACCTGGT GAAACAGTCA CACTCACTTG     240

TCGCTCAAGT ACTGGGGCTG TTACAACTAG TAACTATGCC AACTGGGTCC AAGAAAAACC     300

AGATCATTTA TTCACTGGTC TAATAGGTGG TACCAACAAC CGAGCTCCAG GTGTTCCTGC     360

CAGATTCTCA GGCTCCCTGA TTGGAGACAA GGCTGCCCTC ACCATCACAG GGCACAGAC      420

TGAGGATGAG GCAACATATT TCTGTGCTCT ATGGTACAGC AACCATTGGG TGTTCGGTGG     480

AGGAACCAAA CTGACTGTCC TAGGTGAGTC ACTGGTCCCT CCTTTGCGGC CGCTGAT        537
```

(2) INFORMATION FOR SEQ ID NO: 2:

(i) SEQUENCE CHARACTERISTICS:
        (A) LENGTH: 128 amino acids

```
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 2:

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Thr Tyr Phe Cys Ala Leu Trp
            100                 105                 110

Tyr Ser Asn His Trp Val Phe Gly Gly Gly Thr Lys Leu Thr Val Leu
            115                 120                 125

(2) INFORMATION FOR SEQ ID NO: 3:

(i) SEQUENCE CHARACTERISTICS:
            (A) LENGTH: 554 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 3:

GATCGTCGAC GGACTCAGCA TGGACATGAG GACCCCTGCT CAGTTTCTTG GAATCTTGTT      60

GCTCTGGTTT CCAGGTAAAA TGAACTAAAA TGGGAATGTC ACTGTGATTA GTGTTGATTG     120

GCATTTGGGA GATTTTATCT TTTATGATGC TTACCTATGT AGATACTCAT TATGTCTCCA     180

TTCCTAGGTA TCAAATGTGA CATCAAGGTG ACCCAGTCTC CATCTTCCAT GTATGCATCT     240

CTAGGAGAGA GAGTCACTAT CACTTGCAAG GCGAGTCAGG ACATTAATAA CTATTTAAAC     300

TGGTTCCAGC AGAAACCAGG GAAATCTCCT AAGACCCTGA TCTATCGTGC AAACAGATTG     360

CTAGATGGGG TCCCATCAAG GTTCAGTGGC AGTGGATCTG GGCAAGATTA TTCTCTCACC     420

ATCAGCAGCC TGGAGTATGA AGATATGGGA ATTTATTATT GTCTACAGTT TGACGAGTTT     480

CCGTACACGT TCGGAGGGGG GACCAAGCTG GAAATAAAAC GTAAGTAGTC TTCTCAACTC     540

TTGCGGCCGC TGAT                                                      554

(2) INFORMATION FOR SEQ ID NO: 4:

(i) SEQUENCE CHARACTERISTICS:
            (A) LENGTH: 127 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO: 4:

Met Arg Thr Pro Ala Gln Phe Leu Gly Ile Leu Leu Leu Trp Phe Pro
```

```
1               5                   10                  15
Gly Ile Lys Cys Asp Ile Lys Val Thr Gln Ser Pro Ser Ser Met Tyr
                20                  25              30

Ala Ser Leu Gly Glu Arg Val Thr Ile Thr Cys Lys Ala Ser Gln Asp
            35                  40                  45

Ile Asn Asn Tyr Leu Asn Trp Phe Gln Gln Lys Pro Gly Lys Ser Pro
        50                  55                  60

Lys Thr Leu Ile Tyr Arg Ala Asn Arg Leu Leu Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Gln Phe Asp
            100                 105                 110

Glu Phe Pro Tyr Thr Phe Gly Gly Gly Thr Lys Leu Glu Ile Lys
        115                 120                 125
```

(2) INFORMATION FOR SEQ ID NO: 5:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GATCGTCGAC TTCCAGCTCT CAGAGATGGA GACAGACACA CTCCTGTTAT GGGTACTGCT    60

GCTCTGGGTT CCAGGTGAGA GTGCAGAGAA GTGTTGGATG CAACCTCTGT GGCCATTATG   120

ATACTCCATG CCTCTCTGTT CTTGATCACT ATAATTAGGG CATTTGTCAC TGGTTTTAAG   180

TTTCCCCAGT CCCCTGAATT TTCCATTTCC TCAGAGTGAT GTCCAAAATT CTTCTTAAAA   240

ATTTAAATCA AAAGGTCCTC TGCTGTGAAG TCTTTTATAC ATATATAACA ATAATCTTTG   300

TGTTTATCAT TCCAGGTTCC ACTGGTGACA TTGTGCTGAC ACAGTCTCCT GCTTCCTTAG   360

CTGTATCTCT GGGGCAGAGG GCCACCATCT CATACAGGGC CAGCAAAAGT GTCAGTACAT   420

CTGGCTATAG TTATATGGCG TGGAACCAAC AGAAACCAGG ACAGCCACCC AGACTCCTCA   480

TCTATCTTGT ATCCAACCTA GAATCTGGGG TCCCTGCCAG GTTCAGTGGC AGTGGGTCTG   540

GGACAGACTT CACCCTCAAC ATCCATCCTG TGGAGGAGGA GGATGCTGCA ACCTATTACT   600

GTCAGCACAT TAGGGAGCTT ACACGTTCGG AGGGGGGACC AAGCTGGAAA TAAAACGTAA   660

GTAGTCTTCT CAACTCTTGC GGCCGCTGAT                                   690
```

(2) INFORMATION FOR SEQ ID NO: 6:

(i) SEQUENCE CHARACTERISTICS:
        (A) LENGTH: 128 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 6:

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25              30
```

Val Ser Leu Gly Gln Arg Ala Thr Ile Ser Tyr Arg Ala Ser Lys Ser
         35                  40                  45

Val Ser Thr Ser Gly Tyr Ser Tyr Met Ala Trp Asn Gln Gln Lys Pro
         50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                 85                  90                  95

Leu Asn Ile His Pro Val Glu Glu Asp Ala Ala Thr Tyr Tyr Cys
             100                 105                 110

Gln His Ile Arg Glu Leu Thr Arg Ser Glu Gly Gly Pro Ser Trp Lys
         115                 120                 125

(2) INFORMATION FOR SEQ ID NO: 7:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
GATCGTCGAC CTCAAGGTCC TTACAATGAA ATGCAGCTGG GTCATCTTCT TCCTGATGGC      60

AGTGGTTACA GGTAAGGAGC TCCCAAGTCC CAAACTTGAG GGGCCATACA CTCTGTGACA     120

GTGGCAGTCA CTTTGCCTTT CTTTCTACAG GGTCAATTC AGAGGTTCAG CTGCAGCAGT      180

CTGGGGCTGA GCTTGTGAGG CCAGGGGCCT TAGTCAAGTT GTCCTGCAAA GCCTCTGGCT     240

TCAACATTAA AGACTACTAT ATGTACTGGG TAAAACAGAG GCCTGAACAG GGCCTGGAGT     300

GGATTGGATG GATTGATCCT GAAAATGGTA ATACTGTTTA TGACCCGAAG TTCCAGGGCA     360

AGGCCAGTAT AACAGCAGAC ACATCCTCCA ACACAGCCTA CCTGCAGCTC AGCAGCCTGG     420

CATCTGAGGA CACTGCCGTC TATTACTGTG CTTACTACGG TACTAGCTAC TGGTTTCCTT     480

ACTGGGGCCA AGGGACTCTG GTCACTGTCT CTGCAGGTGA GTCCTACCTT CTCCGCGGCC     540

GCTGAT                                                                546
```

(2) INFORMATION FOR SEQ ID NO: 8:

(i) SEQUENCE CHARACTERISTICS:
        (A) LENGTH: 136 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 8:

Met Lys Cys Ser Trp Val Ile Phe Phe Leu Met Ala Val Val Thr Val
1                5                  10                  15

Asn Ser Glu Val Gln Leu Gln Gln Ser Gly Ala Glu Leu Val Arg Pro
             20                  25                  30

Gly Ala Leu Val Lys Leu Ser Cys Lys Ala Ser Gly Phe Asn Ile Lys
         35                  40                  45

Asp Tyr Tyr Met Tyr Trp Val Lys Gln Arg Pro Glu Gln Gly Leu Glu
         50                  55                  60

Trp Ile Gly Trp Ile Asp Pro Glu Asn Gly Asn Thr Val Tyr Asp Pro
65                  70                  75                  80

```
Lys Phe Gln Gly Lys Ala Ser Ile Thr Ala Asp Thr Ser Ser Asn Thr
                85                  90                  95

Ala Tyr Leu Gln Leu Ser Ser Leu Ala Ser Glu Asp Thr Ala Val Tyr
                100                 105                 110

Tyr Cys Ala Tyr Tyr Gly Thr Ser Tyr Trp Phe Pro Tyr Trp Gly Gln
        115                 120                 125

Gly Thr Leu Val Thr Val Ser Ala
        130             135
```

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GATCGTCGAC CTTGGTTTGT GAATTATG                              28

(2) INFORMATION FOR SEQ ID NO: 10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GATCGTCGAC AGTAGTACCT GCATTATG                              28

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GATCGCGGCC GCAAAGGAGG AGGAGTTAC                             29

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

ATCAGCGGCC GCAAGAAGCA TTAAAGCCAC                            30

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 13:

ATCAGCGGCC GCAAGAAGCT TTGAAACTAC                                              30

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GATCGTCGAC AAATTCAAAK ACAMAAT                                                 27

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GATCGTCGAC AAGACTCAGC CTGACATG                                                28

(2) INFORMATION FOR SEQ ID NO: 16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GATCGTCGAC AAGTTCAAAG ACAAAATG                                                28

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

GATCGTCGAC AGACTCAGCC TGACATG                                                 27

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GATCGTCGAC AGCAGGGGGA GCAGGATG                           28

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GATCGTCGAC AGGGAAAGTT TGAAGATG                           28

(2) INFORMATION FOR SEQ ID NO: 20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GATCGTCGAC ATACATCAGA CCAGCATG                           28

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GATCGTCGAC ATCTAGYTCT CAGAGATG                           28

(2) INFORMATION FOR SEQ ID NO: 22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GATCGTCGAC ATGCATCACA CCAGCATG                           28

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

GATCGTCGAC CACCAAGTTC TCAGAATG                           28

(2) INFORMATION FOR SEQ ID NO: 24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

GATCGTCGAC CAGAGCAGCA GGGACATG                                              28

(2) INFORMATION FOR SEQ ID NO: 25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

GATCGTCGAC CAGGGACAAG TGGGAATG                                              28

(2) INFORMATION FOR SEQ ID NO: 26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GATCGTCGAC CATTCAGAAC TCAGCATG                                              28

(2) INFORMATION FOR SEQ ID NO: 27:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

GATCGTCGAC GCGAGTCAGA CCAGCATG                                              28

(2) INFORMATION FOR SEQ ID NO: 28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GATCGTCGAC GGACACAGTT TAGATATG                                              28

(2) INFORMATION FOR SEQ ID NO: 29:

(i) SEQUENCE CHARACTERISTICS:

(A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

GATCGTCGAC GGACTCAGCA TGGACATG                                              28

(2) INFORMATION FOR SEQ ID NO: 30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

GATCGTCGAC GGAGACGTTG TAGAAATG                                              28

(2) INFORMATION FOR SEQ ID NO: 31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

GATCGTCGAC GGATACACCA TCAGCATG                                              28

(2) INFORMATION FOR SEQ ID NO: 32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

GATCGTCGAC GGCAARGGCA TCAAGATG                                              28

(2) INFORMATION FOR SEQ ID NO: 33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

GATCGTCGAC GGCAGKGGRA GCAAGAT                                               27

(2) INFORMATION FOR SEQ ID NO: 34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

GATCGTCGAC GGTCACAGCA CAAACATG                                      28

(2) INFORMATION FOR SEQ ID NO: 35:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 35:

GATCGTCGAC GGTTGCCTCC TCAAAATG                                      28

(2) INFORMATION FOR SEQ ID NO: 36:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 36:

GATCGTCGAC GTTCATTTCC TCAAAATG                                      28

(2) INFORMATION FOR SEQ ID NO: 37:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 37:

GATCGTCGAC TATCAAGTTC TCAGAATG                                      28

(2) INFORMATION FOR SEQ ID NO: 38:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 38:

GATCGTCGAC TCTCAAGTTC TCAGAATG                                      28

(2) INFORMATION FOR SEQ ID NO: 39:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 39:

```
GATCGTCGAC TCTTGTGAAT TAATCATG                                          28
```

(2) INFORMATION FOR SEQ ID NO: 40:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

```
GATCGTCGAC TGAAAACACA CAGACATG                                          28
```

(2) INFORMATION FOR SEQ ID NO: 41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

```
GATCGTCGAC TGATAAAGCC AAGGAATG                                          28
```

(2) INFORMATION FOR SEQ ID NO: 42:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

```
GATCGTCGAC TGATCACACA CAGWCATG                                          28
```

(2) INFORMATION FOR SEQ ID NO: 43:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

```
GATCGTCGAC TTCCAGCTCT CAGAGATG                                          28
```

(2) INFORMATION FOR SEQ ID NO: 44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

```
ATCAGCGGCC GCAGAGASTT TGGATTCTAC                                        30
```

(2) INFORMATION FOR SEQ ID NO: 45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 45:

ATCAGCGGCC GCAAGAGTTG AGAAGACTAC                           30

(2) INFORMATION FOR SEQ ID NO: 46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 46:

ATCAGCGGCC GCAGTTGAGC AAAAATGTAC                           30

(2) INFORMATION FOR SEQ ID NO: 47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 47:

ATCAGCGGCC GCAAATGAGC AAAARTCTAC                           30

(2) INFORMATION FOR SEQ ID NO: 48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 48:

ATCAGCGGCC GCAAGATGAG AAAAGTGTAC                           30

(2) INFORMATION FOR SEQ ID NO: 49:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 49:

GATCGTCGAC ACACAGACTC ACACCATG                             28

(2) INFORMATION FOR SEQ ID NO: 50:

(i) SEQUENCE CHARACTERISTICS:
        (A) LENGTH: 28 base pairs

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 50:

GATCGTCGAC ACACAGGACC TCACCATG                                              28

(2) INFORMATION FOR SEQ ID NO: 51:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 51:

GATCGTCGAC ACACAGGATC TCACCATG                                              28

(2) INFORMATION FOR SEQ ID NO: 52:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 52:

GATCGTCGAC ACACAGGGCA TTGCCATG                                              28

(2) INFORMATION FOR SEQ ID NO: 53:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 53:

GATCGTCGAC ACACTGACTC AAAACATG                                              28

(2) INFORMATION FOR SEQ ID NO: 54:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 54:

GATCGTCGAC ACACTGACTC AAACCATG                                              28

(2) INFORMATION FOR SEQ ID NO: 55:

(i) SEQUENCE CHARACTERISTICS:
            (A) LENGTH: 28 base pairs
            (B) TYPE: nucleic acid
            (C) STRANDEDNESS: single
            (D) TOPOLOGY: linear
```

(ii) MOLECULE TYPE: DNA (xi) SEQUENCE DESCRIPTION: SEQ ID NO: 55:

GATCGTCGAC ACACTGACTC ACACCATG                                               28

(2) INFORMATION FOR SEQ ID NO: 56:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

GATCGTCGAC ACACTGACTC CAACCATG                                               28

(2) INFORMATION FOR SEQ ID NO: 57:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

GATCGTCGAC ACACTGACTC TAACCATG                                               28

(2) INFORMATION FOR SEQ ID NO: 58:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

GATCGTCGAC ACACTGACTC TCACCATG                                               28

(2) INFORMATION FOR SEQ ID NO: 59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 59:

GATCGTCGAC ACACTGACTT CACCATG                                                27

(2) INFORMATION FOR SEQ ID NO: 60:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

GATCGTCGAC ACATAGACTC TAACCATG     28

(2) INFORMATION FOR SEQ ID NO: 61:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

GATCGTCGAC ACATTGACTC AAACCATG     28

(2) INFORMATION FOR SEQ ID NO: 62:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

GATCGTCGAC AGCCTCCATC AGAGCATG     28

(2) INFORMATION FOR SEQ ID NO: 63:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

GATCGTCGAC AGCCTCCGTC AGAGCATG     28

(2) INFORMATION FOR SEQ ID NO: 64:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

GATCGTCGAC ATTATAACAT TGAACATG     28

(2) INFORMATION FOR SEQ ID NO: 65:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

GATCGTCGAC CAAGTCTTAG ACATCATG     28

(2) INFORMATION FOR SEQ ID NO: 66:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 66:

GATCGTCGAC CACACATCCC TTACCATG                                           28

(2) INFORMATION FOR SEQ ID NO: 67:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 67:

GATCGTCGAC CACAGACACC TCACCATG                                           28

(2) INFORMATION FOR SEQ ID NO: 68:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 68:

GATCGTCGAC CACAGACCMC TCACCATG                                           28

(2) INFORMATION FOR SEQ ID NO: 69:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 69:

GATCGTCGAC CACAGACCTG TCAACATG                                           28

(2) INFORMATION FOR SEQ ID NO: 70:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 70:

GATCGTCGAC CACAGACCTG TCACCATG                                           28

(2) INFORMATION FOR SEQ ID NO: 71:

(i) SEQUENCE CHARACTERISTICS:
        (A) LENGTH: 28 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO: 71:

GATCGTCGAC CACGGAACCC TCACCATG                                              28

(2) INFORMATION FOR SEQ ID NO: 72:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 72:

GATCGTCGAC CACGGACCCC TCACCATG                                              28

(2) INFORMATION FOR SEQ ID NO: 73:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 73:

GATCGTCGAC CACGGACCCC TCACGATG                                              28

(2) INFORMATION FOR SEQ ID NO: 74:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 74:

GATCGTCGAC CACTCGACTC TAACCATG                                              28

(2) INFORMATION FOR SEQ ID NO: 75:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 75:

GATCGTCGAC CACTGGTGTG CAGTCATG                                              28

(2) INFORMATION FOR SEQ ID NO: 76:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 76:

GATCGTCGAC CACTTCTTAG ACATCATG                28

(2) INFORMATION FOR SEQ ID NO: 77:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

GATCGTCGAC CAGAGTCCAC TCRCCATG                28

(2) INFORMATION FOR SEQ ID NO: 78:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

GATCGTCGAC CCTGTCACTG ACTTCATG                28

(2) INFORMATION FOR SEQ ID NO: 79:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 79:

GATCGTCGAC CTCAAGGTCC TTACAATG                28

(2) INFORMATION FOR SEQ ID NO: 80:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 80:

GATCGTCGAC CTCCAGGTCC TTACAATG                28

(2) INFORMATION FOR SEQ ID NO: 81:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 81:

GATCGTCGAC CTCAGTCCTG TCACCATG                28

(2) INFORMATION FOR SEQ ID NO: 82:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 82:

GATCGTCGAC CTCAGTCCTG TCACTATG                                      28

(2) INFORMATION FOR SEQ ID NO: 83:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

GATCGTCGAC GCAGAGGACC TCACAATG                                      28

(2) INFORMATION FOR SEQ ID NO: 84:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

GATCGTCGAC GCCTTTACAG ACTTCATG                                      28

(2) INFORMATION FOR SEQ ID NO: 85:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

GATCGTCGAC GGACCTCACC ATGGGATG                                      28

(2) INFORMATION FOR SEQ ID NO: 86:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 86:

GATCGTCGAC GGGTGTTGCC TAAGGATG                                      28

(2) INFORMATION FOR SEQ ID NO: 87:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 87:

GATCGTCGAC GGTGTWGCCT AAAAGATG                28

(2) INFORMATION FOR SEQ ID NO: 88:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 88:

GATCGTCGAC GGTGTTGCCT AAAGGATG                28

(2) INFORMATION FOR SEQ ID NO: 89:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 89:

GATCGTCGAC GTTGTAGCCT AAAAGATG                28

(2) INFORMATION FOR SEQ ID NO: 90:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 90:

GATCGTCGAC TCAGTCCTTG TCACTATG                28

(2) INFORMATION FOR SEQ ID NO: 91:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 91:

ATCAGCGGCC GCAAAGAAAA AAGCCAGCTT AC            32

(2) INFORMATION FOR SEQ ID NO: 92:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 92:

ATCAGCGGCC GCGAGGTTKT AAGGACTCAC					30

(2) INFORMATION FOR SEQ ID NO: 93:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

ATCAGCGGCC GCGGAGAART TAGGACTCAC					30

(2) INFORMATION FOR SEQ ID NO: 94:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

ATCAGCGGCC GCGGAGAAGK TAGGACTCAC					30

(2) INFORMATION FOR SEQ ID NO: 95:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

ATCAGCGGCC GCTGGAGAGG CCATTCTTAC					30

(2) INFORMATION FOR SEQ ID NO: 96:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

GTCAGTTTGG TTCCTCCAC					19

(2) INFORMATION FOR SEQ ID NO: 97:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

GTGACCTTGG TTCCACCGC                                                    19

(2) INFORMATION FOR SEQ ID NO: 98:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

GTGACCTTGG TTCCACTGC                                                    19

(2) INFORMATION FOR SEQ ID NO: 99:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

GTCAATCTGG TTCCACCTC                                                    19

(2) INFORMATION FOR SEQ ID NO: 100:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 100:

GTGCCTCCAC CGAACGTCC                                                    19

(2) INFORMATION FOR SEQ ID NO: 101:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 101:

GTCCCCCCTC CGAACGTGT                                                    19

(2) INFORMATION FOR SEQ ID NO: 102:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

GTCCCATCAC TGAATGTGA                                                    19

(2) INFORMATION FOR SEQ ID NO: 103:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 103:

GTCCCCGAGC CGAACGTGA                                     19

(2) INFORMATION FOR SEQ ID NO: 104:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 104:

GTCCCAGCAC CGAACGTGA                                     19

(2) INFORMATION FOR SEQ ID NO: 105:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 105:

GACCGTGGTC CCTGCGCCC                                     19

(2) INFORMATION FOR SEQ ID NO: 106:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 106:

GAGAGTGGTG CCTTGGCCC                                     19

(2) INFORMATION FOR SEQ ID NO: 107:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 107:

GACCAGAGTC CCTTGGCCC                                     19

(2) INFORMATION FOR SEQ ID NO: 108:

(i) SEQUENCE CHARACTERISTICS:

-continued

```
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 108:

GACTGAGGTT CCTTGACCC                                                19
```